US005700779A

United States Patent [19]
Goodfellow et al.

[11] Patent Number: 5,700,779
[45] Date of Patent: Dec. 23, 1997

[54] BRADYKININ ANTAGONIST PEPTIDES INCORPORATING N-SUBSTITUTED GLYCINES

[75] Inventors: Val S. Goodfellow, Westminster, Colo.; Manoj V. Marathe, Pittsburgh, Pa.; Eric T. Whalley, Golden, Colo.; Timothy D. Fitzpatrick, Boulder, Colo.; Karen G. Kuhlman, Denver, Colo.

[73] Assignee: Cortech, Inc., Denver, Colo.

[21] Appl. No.: 668,100

[22] Filed: Jun. 20, 1996

Related U.S. Application Data

[63] Continuation of Ser. No. 208,115, Mar. 9, 1994, abandoned.
[51] Int. Cl.$^6$ .................................................. C07K 7/18
[52] U.S. Cl. .................... 514/14; 514/15; 514/21; 530/314; 530/327; 530/328
[58] Field of Search .................... 514/14, 15, 21; 530/314, 327, 328

[56] References Cited

U.S. PATENT DOCUMENTS

| | | | |
|---|---|---|---|
| 4,242,329 | 12/1980 | Claeson et al. | 424/177 |
| 4,693,993 | 9/1987 | Stewart et al. | 514/14 |

FOREIGN PATENT DOCUMENTS

| | | | |
|---|---|---|---|
| 0455133A2 | 4/1991 | European Pat. Off. | |
| WO92/181155 | 10/1992 | WIPO | |
| 9311789 | 6/1993 | WIPO | 514/14 |

OTHER PUBLICATIONS

Raymond J. Vavrek, et al., "Bradykinin Antagonists do not Require a D–aromatic Amino Acid Residue at Position 7", *In Recent Progress on Kinins* (Bonner G. et al. eds.) *Agents and Actions Supplementas* 38 (I), Birkhauser: BAsel., 572–581, (1992).

J. D. Young, et al., "Multi–Year, Multi–Center Evaluation of Solid–Phase Peptide Synthesis", *13th American Peptide Symposium, Edmonton, Albert, Canada,* 1088–1090, (Jun. 20, 1993).

*Primary Examiner*—Cecilia J. Tsang
*Assistant Examiner*—Patrick R. Delaney
*Attorney, Agent, or Firm*—Cushman Darby Cushman IP Group of Pillsbury Madison & Sutro LLP

[57] ABSTRACT

The present invention provides bradykinin type peptides containing N-substituted glycines, particularly bradykinin antagonist peptides useful for the treatment of conditions mediated by bradykinin including pain and inflammation.

13 Claims, No Drawings

BRADYKININ ANTAGONIST PEPTIDES INCORPORATING N-SUBSTITUTED GLYCINES

This is a continuation of application Ser. No. 08/208,115 filed on Mar. 9, 1994 entitled BRADYKININ ANTAGONIST PEPTIDES INCORPORATING N-SUBSTITURED GLYCINES, now abandoned.

BACKGROUND OF THE INVENTION

This invention relates to kinins and, more specifically, to bradykinin receptor antagonists.

Bradykinin (BK) is an endogenous peptide hormone released by proteolytic cleavage of kininogen by a group of endopeptidases known as kallikreins. Bradykinins are mediators in eliciting many pathophysiological responses including pain and hyperalgesia via stimulation of peripheral A- and C-fiber neurons. There is evidence that BK plays an important role in inflammatory response and is a significant mediator in several disease states including hypotension associated with sepsis and bronchopulmonary disorders including asthma.

BK antagonists are considered to be useful in preventing or reducing the action of BK with consequent elimination of, or reduction in the disorders referred to above. There is also compelling evidence that bradykinin antagonists may be useful in the treatment of edema (swelling) in head trauma, edema and pain from severe burns, migraine pain, and pain associated with surgical procedures or cancer.

Bradykinin is a nonapeptide of the sequence $Arg^1$-$Pro^2$-$Pro^3$-$Gly^4$-$Phe^5$-$Ser^6$-$Pro^7$-$Phe^8$-$Arg^9$. The numbering used here is currently employed in the field to compare related sequences of agonists or antagonists to the parent structure of bradykinin. K. G. Claeson and coworkers (U.S. Pat. No. 4,242,329) demonstrated that truncated peptides of the bradykinin sequence containing D-phenylalanine or D-proline replacements for $Pro^7$ exhibited modest but measurable bradykinin antagonist activity. Stewart incorporated D-Phe in the 7 position of the bradykinin peptide sequence which resulted in peptides with antagonist activity on bradykinin receptors (U.S. Pat. No. 4,801,613). Although theoretically interesting, these compounds lacked sufficient potency and in vivo stability to function as viable pharmaceutical agents.

G. Breipohl and collaborators at Hoechst (EPA 0 455 133 A2) and D. Kyle and coworkers at Scios-Nova (PCT/US92/03031) have developed highly potent bradykinin antagonists which incorporate either D-Tic, D-cyclohexylalanine or substituted D-proline analogs at position 7 of the bradykinin sequence. The compounds which Hoechst synthesized contain D-$Tic^7$ and must contain a heterocyclic amino acid at position 8, in which, the α-amino acid nitrogen and α-carbon are incorporated in a heterocyclic ring. Examples of such residues include L-Oic or L-Tic, among others. Kyle synthesized compounds which incorporated similar heterocycles or substituted 4-hydroxyproline or substituted 4-thioproline residues at position 8. Young and collaborators have incorporated N-benzylglycine into position 7 of the bradykinin sequence and have obtained peptides with moderate bradykinin receptor agonist activity (Thirteenth American Peptide Symposium, Edmonton, Alberta, Jun. 20, 1993).

Notwithstanding prior efforts, there remains a considerable need to provide new and improved BK antagonists with useful antagonist properties. The main object of the present invention is to provide such antagonists which include N-substituted glycine in the peptide chain.

Potent bradykinin antagonists utilizing N-substituted glycines as contemplated herein have not been reported previously.

SUMMARY OF THE INVENTION

The present invention provides bradykinin peptide antagonists containing one or more amino acid residues which are N-substituted glycines, in which the N-substituent is an alkyl, cycloalkyl, heterocyclic, aromatic, or heteroaromatic group. These compounds have been shown to be highly potent antagonists of bradykinin and have demonstrated excellent stability and duration of action in vivo. As potent antagonists of bradykinin, the compounds of the invention are considered to be useful for the treatment of conditions mediated by bradykinin including: pain, inflammation, edema, edema associated with head injury, bites and stings, migraine, SIRS/sepsis, chronic inflammatory diseases, burns, small-cell carcinomas, airway hypersensitivity and airway inflammation associated with asthma.

DETAILED DESCRIPTION OF THE INVENTION

Broadly defined, the bradykinin receptor antagonists of the invention are peptides which include one or more N-substituted glycine residues.

More specifically, the invention contemplates bradykinin receptor antagonists of the following formula (I)

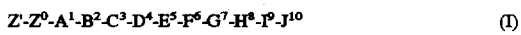

$$Z'\text{-}Z^0\text{-}A^1\text{-}B^2\text{-}C^3\text{-}D^4\text{-}E^5\text{-}F^6\text{-}G^7\text{-}H^8\text{-}I^9\text{-}J^{10} \qquad (I)$$

wherein:

Z' is optionally absent but, if present, is hydrogen, acetyl, adamantylcarboxyl, adamantylacetyl, (C1 to C8)-alkyl, alkanoyl, arylsulfonyl, alkoxycarbonyl or a derivative of a dihydroquinuclidinyl-carboxylic acid;

$Z^0$ may be optionally present or $Z^0$ and $A^1$, which may be the same or different, represent a direct bond, hydrogen, an amino acid residue derived from: D or L arginine, D or L lysine, D or L ornithine, or $H_2N(NH=C)NHCH_2CH_2CH_2(CH_2)_nOC$— where n=0 to 3, or common replacements for arginine as practiced in the art of medicinal chemistry which produce a positively charged heteroatom at physiological pH, such as analogs or homologs of ornithine, arginine, or lysine containing alkylamine, benzamidine, piperidine, alkylguanidine or alkylphosphonium moieties provided that $Z^0$ is other than a direct bond when Z' is absent; further provided that Z' and $Z^0$ are absent when $A^1$ is $H_2N(NH=C)NHCH_2CH_2CH_2(CH_2)_nCO$— where n=0 to 3; $Z^0$ and Z' are absent when $A^1$ is hydrogen;

$B^2$ and $C^3$, which may be the same or different, are proline, hydroxyproline, safcosine, glycine, serine, threonine, thioproline, N-(methyl)serine, N-(methyl) threonine, N-methylphenylalanine, glycine or NR'CHR"CO where R' and R" are independently hydrogen, alkyl (e.g., C1–C8 straight chain or branched or C3–C8 cycloalkyl), aryl, heteroaryl, or alkyl amino;

$D^4$ is glycine, alanine, or thienylalanine;

$B^2C^3D^4E^5$ may be replaced by —$NH(CH_2)_nCO$— where n is a whole number from 4 to 14;

$E^5$ is phenylalanine, phenylalanine substituted with methyl, glycine, cyclopentylglycine, cyclohexylglycine, cyclohexylalanine, 2-indaneglycine, thienylalanine, N-(2-indane)glycine, or N-substituted glycine, where the substituent is alkyl (C1–C8), cycloalkyl(C3-C8), $CH_2Ar$, $CH_2CH_2Ar$, where Ar is aryl or alkylthienyl, an aromatic amino acid, or an aromatic amino acid substituted at the α-nitrogen or α-carbon with a methyl or ethyl group;

$F^6$ is a neutral, basic or acidic, aliphatic or aromatic amino acid, the side chain of which may be substituted, e.g., substituted serine, or cysteine, the substituent for which is selected from N-(alkyl)-succinimidyl, N-(alkyl) pyrolidinone, alkyl(C1–C20), alkenylalkyl(C2–C20), aryl, or alkylaryl(C7–C20);

$G^7$ is an aromatic amino acid, including, D-Tic, D-Dic, D-phenylalanine, indaneglycine, D-cyclopentylglycine, D-cyclohexylglycine, D-proline or proline substituted at the 3 or 4 position with alkyl, aryl, thioalkyl, thioaryl, oxyalkyl, or oxyaryl; or an N-substituted glycine residue where the substituent is aryl, alkylaryl, —$CH_2R$ or —$CH_2CH_2R$ where R is indane, indole, naphthyl or phenyl;

$H^8$ is an amino acid residue selected from the following structures:

—N—$CHR_2$CO—
|
$R_1$ or

—N—$CHR_2$CO—
|
$(CH_2)_m$
|
$R_1$ where m is an integer of from 1 to 6;

$R_1$ is alkyl(C1–C12, straight chained or branched), cycloalkyl(C3–C8), monocyclic or polycyclic aryl, e.g., phenyl or naphthyl, heteroaryl or heterocyclic containing one or more rings of three to eight atoms selected from carbon, nitrogen, oxygen or sulfur;

$R_1$ may also be substituted cycloalkyl, with one to four substituents selected from amino, benzo, hydroxy, mercapto, mercaptoalkyl, alkyl, oxyalkyl, alkyloxy, carboxyl, halogen, phenyl, trifluoromethyl, trifluoromethoxy, aminoalkyl, alkylamino, or carboxamide; or $R_1$ may also be substituted aryl or heteroaryl containing from one to four substituents selected from amino, phenyl, hydroxy, mercapto, mercaptoalkyl, alkyl, oxyalkyl, alkyloxy, carboxyl, halogen, trifluoromethyl, trifluoromethoxy, aminoalkyl, alkylamino, or carboxamide;

$R_2$ is H, methyl or higher alkyl, (e.g., straight chained or branched alkyl of 1–8 carbon atoms) or an acidic, basic or neutral side-chain (alkyl or aromatic) of an amino acid; $H^8$ may be cis-endo-octahydroindol-2-carbonyl when $G^7$ is an N-substituted glycine;

$I^9$ is absent or is a direct bond, OH, or a basic, acidic, or neutral amino acid, in particular, arginine or lysine or $H_2N(NH=C)NHCH_2CH_2CH_2(CH_2)_n$—NH— where n=0 to 3 or common replacements for arginine as practiced in the art of medicinal chemistry, which produce a positively charged heteroatom at physiological pH, such as analogs or homologs of arginine or lysine containing alkylamines, benzamidines, piperidines, alkylguanidines or alkylphosphonium moieties; provided that $I^9$ is other than OH when $J^{10}$ is present and absent or other than a direct bond when $J^{10}$ is absent; and $J^{10}$ is absent or, if present, is OH, or a basic, acidic, or neutral amino acid, or O—R, or NHR, where R is an alkyl group (straight chain or branched) containing from one to fifteen carbon atoms.

The invention is based on the discovery that incorporation of one or more N-substituted glycine residues into peptide sequences related to bradykinin produces antagonists with substantial bradykinin antagonist activity. In a subsidiary feature, it has also been found that certain peptides containing a N-substituted glycine in the chain show useful agonist activities. However, the invention is primarily concerned with novel peptides including N-substituted glycine in the chain which demonstrate outstanding bradykinin antagonist activities together with other useful properties as shown hereafter.

Importantly, the pharmacological profile of the present compounds is significantly different than those obtained for highly potent compounds such as HOE-140, i.e., the peptide of the formula:

D-Arg-Arg-Pro-Hyp-Gly-Thi-Ser-D-Tic-Oic-Arg.

HOE-140, while extremely potent on bradykinin type 2 ($BK_2$) receptors, is devoid of activity on bradykinin type 1 ($BK_1$) receptors, in many in vitro or in vivo pharmacological profiles. Recent data indicate that activation of the $B_1$ receptor is important in various models of chronic inflammation or persistent hyperalgesic conditions (Dray, A. et al., TIPS, 14 287 (1993)). The preferred compounds of the invention exhibit substantial in vivo activity in a $B_1$ receptor antagonist model (LPS-treated rabbit blood pressure assay). By comparison, HOE-104 is devoid of activity in this assay.

Compounds disclosed herein have economic advantage over prior art compounds in that the N-substituted glycines of the invention are much more economical to synthesize and lack the multiple stereocenters that are involved in the case of complicated and expensive residues such as Oic or 4-substituted hydroxyprolines or thioprolines.

In a preferred embodiment of the invention, highly potent antagonists of the bradykinin receptor can be created by incorporating N-substituted glycine residues at position 7 or 8 of a bradykinin peptide sequence. These compounds differ from the prior art in that they do not contain constrained, heterocyclic amino acids, where the cyclic ring includes the nitrogen of the amino acid residue, such as substituted prolines or octahydro-indole-2-carboxylic acid (Oic). A particularly preferred embodiment comprises compounds which contain N-cyclopentyl-, N-cyclohexyl-, N-aryl- or N-alkylaryl glycine at position 8 in the bradykinin peptide sequences as defined above.

It will be recognized by those skilled in the art that various receptor subtypes within tissues may exist. Consequently the most preferred embodiment for a specific chemotherapy will depend on the disease state targeted for therapeutic intervention and the tissues to which bradykinin antagonists are targeted. These parameters can only be truly investigated by clinical testing in humans, but action on animal tissues and receptor binding information as illustrated in this disclosure can serve as a guide in the selection of active compounds.

As used herein, "bradykinin receptor antagonist" is defined as a molecule which blocks the ability of bradykinin to bind to its receptor or causes the binding of bradykinin to its receptor to be altered in a manner such that effective signal transduction does not occur. An antagonist can be a classical competitive inhibitor or a non-competitive one. Consequently, a receptor antagonist need not bind in the same site or orientation as the native ligand, but it should be demonstrable that the molecule physically interacts with the receptor to impart receptor blocking activity.

Other terms, as used herein, may be defined as follows: A "bradykinin type peptide" is a molecule containing at least one amide bond connecting two α-amino acids, and possesses the ability to bind to mammalian bradykinin receptors. A bradykinin type peptide may be an agonist, partial agonist, antagonist, or devoid of measurable biological activity except measurable binding to mammalian bradykinin receptors at concentrations less than 1 millimolar.

The terms "heteroaromatic" and "heteroaryl" refer to monocyclic or polycyclic aromatic ring systems containing nitrogen, oxygen, or sulfur and include, but are not limited to, pyrrole, pyridine, indole, oxazole, pyrazole, pyrimidine, purine, guanine, adenine, pyrazine, quinoline, isoquinoline, furan, benzofuran, benzoxazole, thiophene, benzothiophene, and thiazole.

The terms "Ar" or "aryl" include phenyl, naphthyl, biphenyl, indane, or fluorene.

"Heterocyclic" refers to one or more rings containing three to eight atoms, including carbon and at least one atom selected from nitrogen, oxygen, or sulfur. These include heteroaromatic structures as defined above, as well as epoxides, oxirane, tetrahydrofuran, tetrahydropyran, aziridine, β-lactams, γ-lactams, piperidine, piperazine, pyrrolidinone, diazapine, azapine, oxazolidine, or oxazolidinone.

Where reference is made above to "alkanoyl" or "alkoxy", it is to be understood that these terms contemplate from 2–8 and 1–8 carbons, respectively. Alkyl substituents referred to above, separately or in combination, e.g., as in this alkyl, may comprise from 1–8 carbons.

The 3 or 4 positions of proline as referred to above may be illustrated as follows As used herein, "arginine substitutes" refers to common replacements for arginine as practiced in the art of medicinal chemistry which produce a positively charged heteroatom at physiological pH. These include, but are not

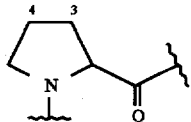

limited to, analogs and homologs of arginine, ornithine or lysine containing akylamines, benzamidine, piperidines, alkylguanidines or alkylphosphonium moieties.

In describing amino acids, the three-letter codes commonly accepted for amino acids as described in European J. Biochemistry 138 9 (1984) have been generally used. However, the use of some of these abbreviations to describe novel N-substituted glycines may cause confusion. Therefore, for the sake of clarity, several abbreviations for certain residues used herein are described below:

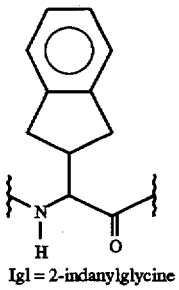

Igl = 2-indanylglycine

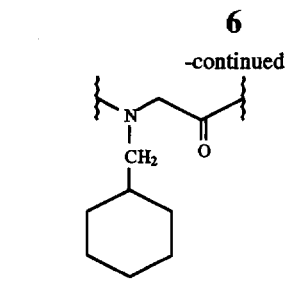

NMch = N-(methylcyclohexyl)glycine

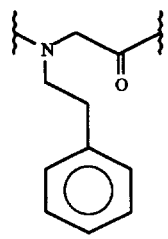

NPeg = N-(phenethyl)glycine

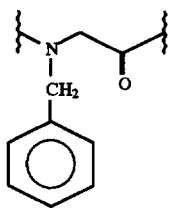

NBng = N-(benzyl)glycine

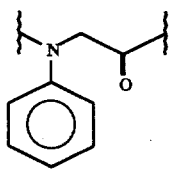

NPhg = N-(phenyl)glycine

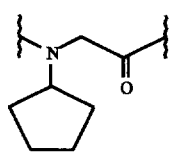

NCpg = N-(cyclopentyl)glycine

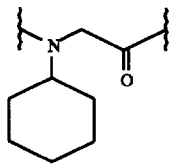

NChg = N-(cyclohexyl)glycine

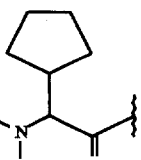

Cpg = cyclopentylglycine

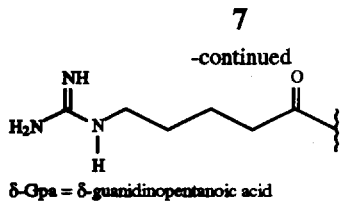

δ-Gpa = δ-guanidinopentanoic acid

Additional abbreviations used in this application are described below:

Boc tert-butyloxycarbonyl
Bop-Cl bis(2-oxo-3-oxazolidinyl)phosphinic chloride
D-Dic dihydroisoquinolin-3-yl-carbonyl
DMF dimethylformamide
Oic cis-endo-octahydroindol-2-carbonyl
PyBrop bromo-tris-pyrrolidino-phosphonium hexafluorophosphate
TFA trifluroacetic acid
Tic 1, 2, 3, 4-tetrahydroisoquinolin-3-yl-carbonyl Peptides according to the invention can be prepared in various conventional ways as will be understood by those in the art. For example, many of the peptides can be synthesized either by solution or solid phase methodology using procedures which are well known in the art (Stewart, J. et al., *Solid Phase Peptide Synthesis*, Pierce Chemical Company, (1984) (Bodanszky, M. et al., The Practice of Peptide Synthesis, Springer Verlag, 1984. Bodansky, *Principles of Peptide Synthesis*, Springer Verlag, (1984)) (Barany, G. et al., *Int. J. Peptide Protein Res.* 30:705739 (1987)). However, coupling of amino acids to hindered N-substituted glycines can only be accomplished using specialized condensing agents such as Bop-Cl (Tung, R. D. et al., *J. Am. Chem. Soc.* 107 4342 (1985)) or PyBrop (Coste, J., Peptides: Proceedings of the Twenty-first European Peptide Symposium (1990)) or acyl chlorides (Beyermann, M. et al., *J. Org. Chem.* 55, 721–728, (1990)) or acyl fluorides (Carpino, L. A. et al., *J. Am. Chem. Soc.* 112 9652 (1990)) derived from suitably protected amino acids. Solid phase methodologies (Zuckermann, R. N., *J. Am. Chem. Soc.* 114 10646 (1992)) which allow the synthesis of N-substituted glycines by N-alkylation of amines or anilines by α-halocarbonyl compounds are known approaches to synthesizing peptides which contain N-substituted glycines by solid phase synthesis. However, solid phase methodologies which allow the use of the inexpensive and efficient coupling agent Bop-Cl have not been previously reported.

Novel N-substituted glycines or N-substituted amino acids can be synthesized by the following methods:

An amine or aniline of structure $R_1NH_2$ can be reacted with a suitably protected α-halo-acetate of structure A, in a polar solvent such as acetonitrile, dichloromethane, chloroform, tetrahydrofuran, or dimethylformamide with or without the addition of additional base such as tertiary amines, metal hydrides, metal or ammonium carbonates or bicarbonates to produce the N-substituted amino acid B. Protection of the α-amino group by methods well known in the art (T. Greene and P. G. M. Wuts provide examples of numerous protecting groups which are compatible with common techniques applied in peptide synthesis (Greene, T. et al., *Protective Groups in Organic Synthesis*, second edition, John Wiley and Sons, (1991)) provides an amino acid derivative C, suitable for conventional methods of peptide synthesis.

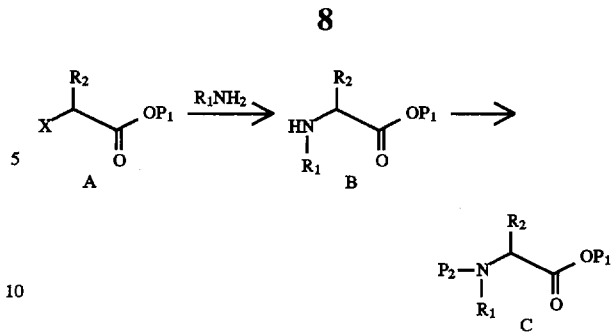

where X=halogen or leaving group, $P_1$ and $P_2$ are protecting groups.

Alternatively, a suitably protected amino acid D can be reacted with a moiety containing a leaving group X such as chloride, bromide, iodide, tosylate, mesylate, triflate etc. to produce B. Protection of the amine by methods well known in the art provides an intermediate for peptide synthesis (See Greene, T., et al., *Protective Groups in Organic Synthesis*, second edition, John Wiley and Sons, (1991)). In limited cases X may be displaced by the anion formed by deprotonation of an N-protected (urethane or sulfonamide based protecting group) amino acid by a strong base such as NaH to produce C directly by alkylation of the anion.

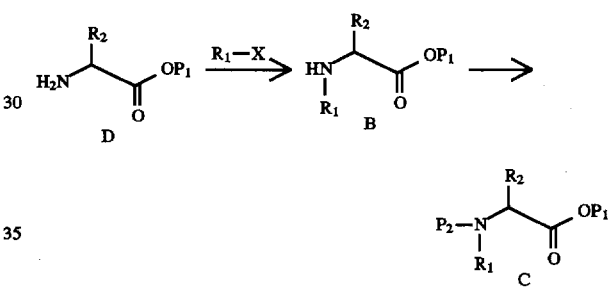

where X=halogen or leaving group, $P_1$ and $P_2$ are protecting groups.

Finally, intermediate B may be formed by reductive amination where suitable amines and aldehydes or ketones are condensed to form Schiff's bases or imines, which are then reduced with hydrogen and catalysts or active hydride reagents, such as sodium cyanoborohydride or sodium borohydride, to the desired amine B. Protection of the amine by methods well known in the art provides an intermediate C suitable for peptide synthesis.

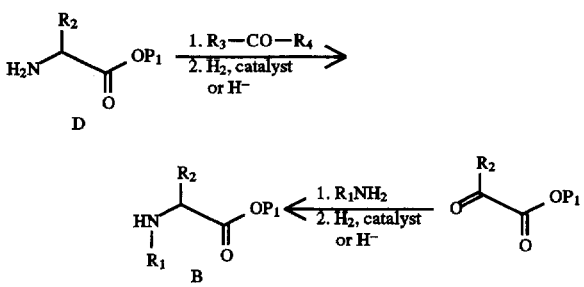

where $P_1$ and $P_2$ are protecting groups and $R_3$—CO—$R_4$ represent a cyclic, or straight chained ketone, or an aldehyde which provide $R_1$ upon reductive amination.

Therapeutic applications of bradykinin antagonists include traumatic, inflammatory or pathological conditions mediated by bradykinins or their closely related metabolites.

These conditions may include treatment of bites, stings, general trauma, head trauma, inflammatory conditions including inflammatory bowel disease, burns, rashes, shock or hypotension associated with sepsis, and pain, especially pain associated with surgical or dental procedures. In addition bradykinin antagonists may be used for the treatment of airway hypersensitivity and inflammation, as well as other symptoms associated with asthma. Bradykinin is recognized as a mitogenic agent and compounds disclosed in this invention have exhibited in vitro activity which may indicate their utility as anti-cancer agents.

The compounds may be administered topically, or by injection or infusion or as an oral suspension in an appropriate vehicle or as tablets, pills, capsules, caplets or the like. The dosage and manner of administration will be defined by the application of the bradykinin antagonist and can be determined by routine methods of clinical testing to find the optimum dose. These doses are expected to be in the range of 0.001 mg/Kg to 100 mg/Kg of active compound.

It will be understood that the compounds of the invention are composed of amino acids which may form salts due to their acidic or basic nature, and any pharmacologically acceptable salt derived from the compounds described herein such as hydrochlorides, acetates, phosphates, maleates, citrates, benzoates, salicylates, succinates, ascorbates and the like, are considered part of the present invention. A common approach in medicinal chemistry is to modify known drug substances which are peptide based to form ester or amide prodrugs which exhibit greater bioavailability and prodrugs derived from the compounds disclosed herein constitute part of the present invention. Methods for designing and preparing prodrugs are described in detail in the medicinal chemical literature (Bundgaard, H., *Design of Prodrugs*, Elsevier (1985)).

The compounds of the invention may be administered together with other pharmacological agents such as kinin antagonists, including neurokinin antagonists, or opioid agonists, protease inhibitors, especially inhibitors of elastase or in combination with other analgesic drugs or anti-cancer drugs.

Representative compounds according to the invention include the following where NBng, NChg, NCpg, NPeg, NMCh and NPhg represent, respectively, N-benzyl glycine, N-cyclohexylglycine, N-cyclopentyl glycine, N-phenylethyl glycine, N-methylcyclohexyl glycine and N-phenylglycine, include the following:

Compound 1
   D-Arg-Arg-Pro-Hyp-Gly-Thi-Ser-NBng-Oic
Compound 2
   D-Arg-Arg-Pro-Hyp-Gly-Thi-Ser-DTic-NChg
Compound 3
   D-Arg-Arg-Pro-Hyp-Gly-Thi-Ser-Igl*-NChg-Arg:*Isomer A
Compound 4
   D-Arg-Arg-Pro-Hyp-Gly-Thi-Ser-Igl*-NChg-Arg *Isomer B
Compound 5
   D-Arg-Arg-Pro-Hyp-Gly-Thi-Ser-D-Tic-NChg-Arg
Compound 6
   D-Arg-Arg-Pro-Hyp-Gly-Thi-Ser-D-NBng-Oic-Arg
Compound 7
   D-Arg-Arg-Pro-Hyp-Gly-Thi-Ser-D-NBng-NChg-Arg
Compound 8
   D-Arg-Arg-Pro-Hyp-Gly-Thi-Ser-D-Tic-NCpg-Arg
Compound 9
   D-Arg-Arg-Pro-Hyp-Gly-Thi-Ser-D-Phe-NChg-Arg
Compound 10
   D-Arg-Arg-Pro-Hyp-Gly-Thi-Ser-D-Cpg-NChg-Arg
Compound 11
   D-Arg-Arg-Pro-Hyp-Gly-Thi-Ser-NPeg-Oic-Arg
Compound 12
   D-Arg-Arg-Pro-Hyp-Gly-Thi-Ser-D-Tic-NMch-Arg
Compound 13
   δ-Gpa-Arg-Pro-Hyp-Gly-Thi-Ser-D-Tic-NChg-Arg
Compound 14
   δ-Gpa-Pro-Hyp-Gly-Thi-Ser-D-Tic-NChg-Arg
Compound 15
   D-Arg-Arg-Pro-Hyp-Gly-Thi-Ser-D-Tic-NPhg-Arg
Compound 16
   D-Arg-Arg-Pro-Hyp-Gly-Thi-Ser-D-Phe-NPhg-Arg
Compound 17
   D-Arg-Arg-Hyp-Hyp-Gly-Thi-Ser-D-Tic-NChg-Arg
Compound 18
   δ-Gpa-Arg-Pro-Hyp-Gly-Thi-Ser-D-Tic-NChg The representative compounds set further above correspond to compounds of formula (I) as follows:

Z' is absent;
Z$^0$ is D-Arg or δ-Gpa or is absent;
A$^1$ is Arg or δ-Gpa;
B$^2$ is Pro or Hyp;
C$^3$ is Hyp;
D$^4$ is Gly;
E$^5$ is Thi;
F$^6$ is Ser;
G$^7$ is NBng, NPeg, NChg or DTic, Igl, D-PHe or DCpg;
H$^8$ is Oic, Arg, NChg, MNch, NPhg, at least one of G$^7$ and H$^8$ being an N-substituted glycine;
I$^9$ is absent or Arg; and
J$^{10}$ is absent.

While the N-substituted glycine residue is illustrated in the foregoing as being in the 7- and/or 8-position of the exemplified peptides (using BK sequence numbering), it will be recognized that the positioning of the N-substituted glycine can be varied. Similarly, other N-substituents and variations than those illustrated can be used according to the invention. For example, useful analogs of the exemplified compounds can be provided by omitting the end Arg group. However, a preferred group of peptides according to the invention comprises compounds having 8–10 amino acids of formula (I) wherein the 7-and/or 8-position (using BK sequence numbering) is an N-substituted glycine, the substituent advantageously being phenyl, benzyl, phenethyl, cycloalkyl such as, cyclopentyl or cyclohexyl, or lower alkyl cyclohexyl such as methyl cyclohexyl.

Another preferred subgroup of compounds according to the invention may be deferred as follows:

D-Arg-Arg-Pro-Hyp-Gly-Thi-Ser-D-Tic-(N-R)Gly-Arg
or
   D-Arg-Arg-Pro-Hyp-Gly-Thi-Ser-D-Tic-(N-R)Gly wherein-R, the substituent of the glycine residue, is cyclohexyl substituted with methyl, ethyl, propyl, isopropyl, methoxy, ethoxy, normal or iso-propyloxy, $CH_2OCH_2CH_3$, $CH_2CH_2O-CH(CH_3)_2$, $CH_2CH_2OCH_3$, $CH_2CH_2OCF_3$, thiomethyl, thioethyl, thiopropyl (normal or isopropyl).

The invention is described further by the following examples where antagonists represent preferred embodiments of the invention. These examples are intended to be illustrative and instructive and are not intended to be limiting.

EXAMPLES

Example I

General Procedure for Synthesis of Exemplified Peptides

Peptides Ending In C-terminal Arginine

All amino acids were protected at the alpha nitrogen with the tert-butoxycarbonyl group. Serine was protected as the benzyl ether. The guanidine of arginine was protected with the tosyl group, unless otherwise stated. No side chain protection was employed for hydroxyproline.

Resin Preparation

PAM resin (generally 0.20 to 2 g, Bachem) prederivatized with Nα-Boc-Ng-p-Tosyl-L-arginine (~0.25 to 0.75 equivalents per gram) was charged in a vessel designed for manual solid phase peptide synthesis (Stewart, J. M. et al., *Solid Phase Peptide Synthesis*, Pierce Chemical Company, (1984). The resin was treated with 25 mL of dry $CH_2Cl_2$, with agitation provided by nitrogen bubbling for one minute. The solution was drained away and washing with $CH_2Cl_2$ was repeated (2×25 mL). A similar wash was repeated with dimethyl formamide (3×25 mL) followed by a wash with dichloromethane (3×25 mL).

Deprotection

The washed resin was treated with 25 mL of a 1:1 mixture of trifluoroacetic acid in dichloromethane. Agitation was maintained for 5 minutes by nitrogen bubbling, then the solvent was filtered away. The resin was again treated with 25 mL of a 1:1 mixture of trifluoroacetic acid in dichloromethane; agitation was maintained for 25 minutes by nitrogen bubbling, then the solvent was filtered away.

Neutralization

The resin was washed sequentially with dichloromethane (3×25 mL), dimethylformamide (2×25 mL) and again with dichloromethane. The resin was washed with a solution of 10% (v/v) diisopropylethylamine in dichloromethane (3×25 mL). To remove traces of base, the resin was washed with dichloromethane (3×25 mL).

Procedure for Coupling with N-Boc-amino acid HOBt esters

Four equivalents of the Boc-protected amino acids were dissolved in a minimum amount of DMF, followed by four equivalents of HOBt (1-hydroxybenzotriazol-monohydrate). To this was added four equivalents of DCC (dicyclohexylcarbodiimide). The reaction stirred at room temperature for one hour. The dicyclohexylurea was removed by filtration and the resulting filtrate was added to the peptide synthesis vessel containing the N-deprotected peptidyl-resin. Agitation was continued for one hour.

Procedure for Coupling Boc-Protected Amino Acids to the Peptidyl Resin Containing an N-terminal, Hindered Secondary Amine Such as D-Tic, Oic, or an N-Substituted Glycine Residue Two equivalents of the Boc-protected amino acid, and two equivalents of diisopropylethylamine were dissolved in a minimum amount of dichloromethane. The solution was chilled to 0° C. under nitrogen and treated with two equivalents of Bop-Cl. The reaction stirred under nitrogen at 0° C. for 3 hours. The homogeneous solution was added to the peptide synthesis vessel containing the N-deprotected peptidyl-resin, followed by an equivalent volume of dimethylformamide containing an additional two equivalents of diisopropylethyl amine. Agitation was continued for two hours. In specific cases identified within specific examples, four equivalents of the activated amino acid were employed by doubling the amount of reagents and solvents used in this procedure.

Post-Coupling Washes

The resin was washed with dimethyl formamide (3×25 mL) followed by dichloromethane (3×25 mL).

Evaluation of Coupling Completion

A few particles of the resin were reacted with ninhydrin using a modification of the method developed by Kaiser (Stewart, J. M. et al., *Solid Phase Peptide Synthesis*, Pierce Chemical Company, (1984)) to qualitatively determine if the reaction had gone to completion. If the reaction was complete, the resin was washed again with dichloromethane and the deprotection and coupling steps were continued as above. If unreacted amine appeared to be present, the resin was again submitted to the neutralization and coupling procedure. N-alkylamino acid residues may give erratic results when subjected to the Kaiser test, in such cases, the use of quantitative amino acid analysis performed after hydrolysis of a small sample of the peptidyl resin may be of value in determining the completion of coupling reactions.

HF Deprotection

The peptide resin was carefully dried and transferred to a vessel especially prepared for HF reactions (Peninsula Laboratories), the peptide was treated with 1 mL of anisole followed by the condensation of approximately 9 mL of HF at low temperature. The reaction was allowed to continue 45–60 minutes at 0° C. and the HF was removed carefully under vacuum. The resin/scavenger mixture was dried under vacuum for one hour, then the residue was carefully washed with anhydrous diethyl ether and the peptide extracted into 10% acetic acid solution. The acetic acid solution was lyophilized to a solid which was purified by reverse phase preparative C18 HPLC chromatography (Dynamax or Vydac 30×2.5 cm, 10 u C18) to give the desired peptides.

Peptides Ending In C-terminal Oic or N-substituted Glycines

The C-terminal Boc-amino acid (1.0 mmol) was dissolved in a mixture of 10 mL 95% Ethanol and 3 mL $H_2O$. Cesium bicarbonate (1 mmol) was added, and the reaction stirred for 1 hour. The solvent was removed in vacuo on a rotary evaporator. Small portions of benzene were added and removed in vacuo to remove traces of water, until a white free-flowing powder was obtained. Merrifield resin (Bachem, 1% cross-linked, 100–200 mesh, ~1 meq/g, 1.0 meq) and the cesium salt were suspended in dry, nitrogen purged, dimethyl formamide (6–8 mL/g of resin) and the reaction stirred under nitrogen at 50° C. for 24 to 36 hours. The solution was filtered and the resin was washed three times, with 50 mL of each of the following solvents in sequential manner: dimethylformamide, 50% dimethylformamide in water, dimethylformamide, and ethanol. The resin was dried overnight. An approximation of the Boc-amino acid substitution density of the resin was made by the mass gained by the resin during derivitization. The Boc-amino acid derivatized resin was prepared for peptide synthesis and deprotected as described above for PAM resins.

Characterization of Peptides

The methods of amino acid analysis used herein provide accurate quantification of commonly occurring amino acids. Quantitation of unusual amino acids often requires extensive methods development. Unusual amino acids such as D-Tic, Oic, and N-substituted glycines can be qualitatively identified by retention time on the amino acid analyzer. Similar remarks apply to peptide sequencing as well. Residues which could be identified qualitatively, but not measured in a quantitative manner, are marked with an asterisk (*). The sequence was found to be correct for all compounds for which data were obtained; these are clearly identified within the detailed experimental text. Specific residues can be identified by peptide sequencing, but quantitation of unusual residues was not carried out. The low-resolution laser-desorption mass spectrometer used for present purposes allows determination of molecular ions with an accuracy of approximately 0.1%. This minor expected limitation in accuracy accounts for the ~1 a.m.u. difference between calculated and observed molecular weights which are reported for a few of the compounds.

EXAMPLE II

Synthesis of Compound 1

D-Arg-Arg-Pro-Hyp-Gly-Thi-Ser-NBng-Oic

N-α-Boc-N-benzylglycine ethyl ester

To a stirred solution of N-benzylglycine ethyl ester (1.0 g, 5.17 mmol, 97.0%) and triethyamine (0.79 mL, 5.7 mmol) in DMF (1.0 mL) was added a solution of di-tert-butyl dicarbonate (1.28 g, 5.7 mmol) in DMF (2.0 ml). The resulting solution was stirred at room temperature under $N_2$ for 19 hours. DMF was evaporated in vacuo and the resulting oil was dissolved in ethyl acetate (50 ml). The ethyl acetate layer was washed with 10% $Na_2CO_3$ solution (2×25 ml), brine (2×30 ml), dried ($MgSO_4$) and the solvent evaporated to give the title compound, (1.48 g, 98.0%) as an oil. $^1H$ NMR ($CDCl^3$), δ 1.2–1.3 (t, 3H), 1.49 (s, 9H), 3.8 (s, 1H), 3.9 (s, 1H), 4.1–4.2 (q, 4H), 4.5–4.55 (d, 2H), 7.2–7.4 (m, 5H); $^{13}C$ NMR ($CDCl_3$); δ13.95, 14.04, 28.06, 28.12, 47.54, 47.93, 50.85, 51.33, 60.70, 80.16, 80.33, 127.22, 127.31, 127.93, 128.36, 137.195, 137.43, 155.40, 155.56, 169.67, 169.71.

N-α-Boc-N-benzylglycine

NaOH (0.3 g, 7.57 mmol) dissolved in minimum amount of water was added to a stirred solution of N-α-Boc-N-benzylglycine ethyl ester (0.74 g, 2.52 mmol) in methanol (5.0 ml). The reaction mixture was stirred at room temperature for 18 hours. Methanol was evaporated in vacuo and the resulting residue was dissolved in water. The aqueous layer was extracted with chloroform (2×50 ml), chilled to 0° C., then the pH was adjusted to 2.0 with 1N HCl and the solution was then extracted with ethyl acetate. The ethyl acetate layer was then washed with brine, dried ($MgSO_4$) and evaporated in vacuo to yield 1.18 g (88.0%) of the title compound. $^1H$ NMR ($CDCl_3$); δ 1.49 (s, 9H), 3.82 (s, 1H), 3.98 (s, 1H), 4.52 (s, 1H), 4.56 (s, 1H), 7.2–7.4 (m, 5H), 11.5 (br S, 1H); $^{13}C$ NMR ($CDCl_3$) δ 28.19, 28.26, 47,43, 47.57, 50.85, 51.49, 80.92, 81.10, 127.46, 127.52, 128.08, 128.6, 136.98, 137.16, 155.58, 155.99, 175.40, 175.70.

Nα-Boc-Oic resin (0.60 g, 0.83 meq/g) was prepared as described above; the peptide was coupled sequentially and cleaved from the resin using the procedures previously described, to provide 91.3 mg of crude material. HPLC purification (10–65% $CH_3CN$, 0.1% TFA, gradient over 55 minutes, 20 mL/min) provided 46.1 mg of compound 1 as a colorless lyophilate. Laser Desorption Mass Spectrum (LD-MS): Calculated 1136 (M+H); Found 1136 (M+H). Amino Acid Analysis (AAA): Arg 2.06 (2), Hyp 0.83 (1), Pro 0.99 (1), Gly 0.99 (1), Thi*, Ser 1.12 (1), NBng*, Oic*. Correct sequence analysis was obtained.

EXAMPLE III

Synthesis of Compound 2

D-Arg-Arg-Pro-Hyp-Gly-Thi-Ser-DTic-NChg

N-(Cyclohexyl)glycine benzyl ester

Cyclohexylamine (14.3 mL, 125 mmol) was dissolved in 50 mL of THF and chilled to 0° C. under nitrogen; to this solution was added, by drop-wise addition, a solution of benzyl 2-bromoacetate (7.93 mL, 50 mmol) in 50 mL of THF. The reaction was allowed to warm to room temperature and was then stirred for approximately 15 hours. The solvent was removed in vacuo and the residue was taken up in 200 mL dichloromethane and washed with 100 mL of 10% sodium carbonate solution. The sodium carbonate solution was extracted twice with 50 mL of dichloromethane. All dichloromethane layers were combined, dried over anhydrous magnesium sulfate, and concentrated in vacuo. The residue was treated with 26 mL of 4N HCl in dioxane, volatiles were removed in vacuo, and the residue was triturated with cold, anhydrous diethylether. The solid was collected and dried for several hours under reduced pressure to yield 15 g of the hydrochloride salt contaminated with traces of cyclohexylamine hydrochloride. This mixture was dissolved in 300 mL of dichloromethane and the solution was washed with 100 mL of 10% sodium carbonate solution. The aqueous solution was back-extracted with dichloromethane. All dichloromethane layers were combined, dried over magnesium sulfate and dried under high vacuum (~1 torr) to provide 11.63 g of the pure title compound as an oil. $^1H$ NMR ($CDCl_3$) δ 1.0–1.32 (m, 4H); 1.55–1.78 (m, 4H); 1.83 (m, 2H); 2.41 (tt, J=10, 4 Hz, 1H); 3.48 (s, 2H); 5.17 (s, 2H); 7.36 (s, 5H); $^{13}C$ NMR (DMSO) δ 24.62, 25.82, 33.08, 48.02, 56.12, 66.28, 128.15, 128.36, 135.47, 142.53.

Boc-N-(cyclohexyl)glycine benzyl ester

N-(Cyclohexyl)glycine benzyl ester was dissolved in 44.4 mL of dioxane and 44.4 mL of 1N NaOH solution were added, followed by di-tert-butyl dicarbonate (10.68 g). Stirring was continued for approximately 15 hours, after which volatiles were removed by roto-evaporation. The resulting residue was partitioned between 100 mL water and 100 mL ethyl acetate. The layers were separated and the aqueous layer was acidified to pH 3 with 5% potassium bisulfate solution. The aqueous layer was then extracted with ethyl acetate and all ethyl acetate solutions were combined and washed with saturated sodium bicarbonate solution, saturated sodium chloride solution and dried over magnesium sulfate. Removal of the solvent by rotary evaporation and further drying under high vacuum provided 14.50 g of the title compound as an oil. $^1H$ NMR ($CDCl_3$) β 0.95–1.55 (m, 14H); 1.63 (m, 1H); 1.77 (m, 4H); 3.70–4.1 (m, 3H); 5.16 (s, 2H); 7.36 (s, 5H).

Boc-N-(cyclohexyl)glycine

Boc-N-(cyclohexyl)glycine benzyl ester (14.0 g, 40 mmol) was dissolved in 240 mL anhydrous ethanol, flushed with dry nitrogen and combined carefully under inert atmosphere with 1.5 g of 10% palladium on carbon. Using a Parr apparatus the nitrogen atmosphere was replaced with hydrogen (43 P.S.I.) and the mixture was shaken over 24 hours at room temperature. The mixture was purged with nitrogen and the catalyst and solids were removed by filtration through a pad of celite. The filtrate was concentrated by rotary evaporation and the residue was taken up in 300 mL of ethyl acetate. The ethyl acetate layer was extracted with 150 mL of 1N sodium hydroxide solution. The basic solution was acidified in an ice bath to pH 3 with 1N hydrochloric acid solution. The acid solution was extracted with ethyl acetate (3×100 mL). This solution was washed with saturated sodium chloride solution and concentrated in vacuo to a colorless oil which was further dried under high vacuum. The resulting glass/solid was triturated with hexane, which after filtration and drying provided the title compound (8.89 g) as a colorless powder. M.P. 103–104 C (uncorr.) Anal. ($C_{13}H_{23}NO_4$) C, H, N; C: calcd., 60.68; found, 60.77 H; calcd., 9.01; found, 9.20. N: calcd., 5.44; found, 5.44.

¹H NMR (CDCl₃) δ 1.07 (m, 1H); 1.10–1.55 (m, 4H); 1.43 (s, 9H ), 1.55–1.9 (m, 5H); 3.67–4.13 (m, 3H); 11.33 (br s, 1H); ¹³C NMR (CDCl₃) δ 25.43, 25.68, 28.20, 30.91, 44.03, 44.26, 44.36, 44.42, 54.03, 54.18, 56.13, 80.36, 80.47, 154.81, 176.83.

Nα-Boc-NChg resin (0.63 g, 0.79 meq/g) was prepared as described above. The peptide was coupled sequentially and cleaved from the resin using the procedures previously described, to provide 71 mg of crude material. HPLC purification (10–65% CH₃CN, 0.1% TFA, gradient over 55 minutes, 20 mL/min) provided 23 mg of compound 2 as a colorless lyophilate. LD-MS: Calc. 1136.6 (M+1); Found 1136.5 (M+1). AAA: Arg 2.01 (2), Hyp 0.81 (1), Pro 0.94 (1), Gly 0.98 (1), Thi*, Ser 1.27 (1), NChg*, Tic*. Correct sequence analysis was obtained.

EXAMPLE IV

Synthesis of Compound 3 and Compound 4

D-Arg-Arg-Pro-Hyp-Gly-Thi-Ser-Igl*-NChg-Arg

*Isomers A and B
(D,L)-N-(BOC)-2-indaneglycine (D,L)-2-Indaneglycine was prepared by the method of Porter and Shive (Porter, T. H. and Shive, W., *J. Med. Chem.* 11 402 (1968)). D,L-2-Indaneglycine (3.36 g, 17.54 mmols) was dissolved in a mixture of dioxane (30 mL) and water (15 mL) containing sodium hydroxide (1.76 g, 1.1 equivalent). Di-tert-butyl dicarbonate (4.35 g, 19.3 mmol) was added. The reaction stirred 18 hours at room temperature. Volatiles were removed on the rotary evaporator and the aqueous remainder was extracted with chloroform and then acidified to pH 2–3, with HCl and extracted with ethyl acetate. The ethyl acetate solution was washed with brine and dried over anhydrous magnesium sulfate. Removal of the solvent provided 2.87 g (56%) of (D,L)-N-(Boc)-2-indaneglycine.

Boc-Ng-p-Tosyl-L-arginine PAM resin (1.52 g, Bachem, 1.0 meq) prederivatized with Nα-Boc-Ng-p-Tosyl-L-arginine was charged in a vessel designed for manual solid phase peptide synthesis. The peptide was coupled sequentially and cleaved from the resin using the procedures previously described, to provide 330 mg of crude material. HPLC purification of 100 mg of this crude material (10–65% CH₃CN, 0.1% TFA, gradient over 55 minutes, 20 mL/min) provided 30.4 mg of isomer A (compound 3) and 31.5 mg of isomer B (compound 4). HPLC retention times: (5–55% CH₃CN, 0.1% TFA over 50 minutes, C18 5μ, analytical column) Isomer A (compound 3) 27.9 minutes; Isomer B (compound 4) 28.6 minutes. Compound 3 (Isomer A): LD-MS: Calculated 1306 (M+H); Found 1307 (M+H). AAA: Arg 3.36 (3), Hyp 0.93 (1), Pro 0.90 (1), Gly 0.90 (1), Thi*, Ser 0.91 (1), NChg*, Igl*. Compound 4 (Isomer B) LD-MS: Calculated 1306 (M+H) Found 1305.8 (M+H). AAA: Arg 3.43 (3), Hyp 0.92 (1), Pro 0.89 (1), Gly 0.89 (1), Thi*, Ser 0.91 (1), NChg*, Igl*.

EXAMPLE V

Synthesis of Compound 5 (CP-0597)

D-Arg-Arg-Pro-Hyp-Gly-Thi-Ser-D-Tic-NChg-Arg

Boc-Ng-p-Tosyl-L-arginine PAM resin prederivatized with Nα-Boc-Ng-p-Tosyl-L-arginine was charged in a vessel designed for manual solid phase peptide synthesis. The peptide was coupled sequentially and cleaved from the resin using the procedures previously described, to provide 330 mg of crude material. Four equivalents of preactivated Boc-amino acids were employed throughout the synthesis. HPLC purification of the crude material (10–65% CH₃CN, 0.1% TFA, gradient over 55 minutes, 20 mL/min) provided 131.8 mg of compound 5. HPLC retention time: (5–70% CH₃CN, 0.1% TFA over 65 minutes, C18 5μ, analytical column, R.t.=30.3 min.) LD-MS: Calc 1293; Found 1293 (M+H) Amino Acid Analysis: Arg 3.13 (3), Hyp 0.90 (1), Pro 0.95 (1), Gly 0.98 (1), Thi*, Ser 1.04 (1), NChg*, Tic*. Correct sequence analysis was obtained.

EXAMPLE VI

Synthesis of Compound 6

D-Arg-Arg-Pro-Hyp-Gly-Thi-Ser-D-NBng-Oic-Arg

Nα-Boc-Ng-p-Tosyl-L-arginine PAM resin (0.240 g, Bachem, 0.14 meq) prederivatized with Na-Boc-Ng-p-Tosyl-L-arginine was charged in a vessel designed for manual solid phase peptide synthesis. The peptide was coupled sequentially and cleaved from the resin using the procedures previously described. HPLC purification of a portion of the crude material (5–55% CH₃CN, 0.1% TFA, gradient over 55 minutes, 20 mL/min) provided 8.3 mg of compound 6. HPLC: R.t.=14.0 minutes (20–60% CH₃CN, 0.1% TFA over 30 minutes, C18 5μ, analytical column). LD-MS: Calculated 1293; Found 1293 (M+H). AAA: Arg 2.98 (3), Hyp 1.08 (1), Pro 0.97 (1), Gly 1.10 (1), Thi*, Ser 0.87 (1), NBng*, Oic*. Correct sequence analysis was obtained.

EXAMPLE VII

Synthesis of Compound 7

D-Arg-Arg-Pro-Hyp-Gly-Thi-Ser-D-NBng-NChg-Arg

Boc-Ng-p-Tosyl-L-arginine PAM resin (0,240 g, Bachem, 0.14 meq) prederivatized with Na-Boc-Ng-p-Tosyl-L-arginine was charged in a vessel designed for manual solid phase peptide synthesis. The peptide was coupled sequentially and cleaved from the resin using the procedures previously described. HPLC purification of a portion of the crude material (5–55% CH₃CN, 0.1% TFA, gradient over 55 minutes, 20 mL/min) provided 42 mg of compound 7. HPLC: R.t.=13.5 minutes (20–60% CH₃CN, 0.1% TFA over 30 minutes, C18 5μ, analytical column). LD-MS: Calc. 1280; Found 1280. AAA: Arg 3.03 (3), Hyp 1.06 (1), Pro 0.99 (1), Gly 1.02 (1), Thi*, Ser 0.90 (1), NBng*, NChg*. Correct sequence analysis was obtained.

EXAMPLE VIII

Synthesis of Compound 8

D-Arg-Arg-Pro-Hyp-gly-Thi-Ser-D-Tic-NCpg-Arg

N-Cyclopentylglycine benzyl ester

A solution of Benzyl-2-bromoacetate (3.30 ml, 20.0 mmol) in 20 mL CH₂Cl₂ was added drop-wise to a solution of cyclopentylamine (8.60 g, 100 mmol) in 20 mL of CH₂Cl₂, with stirring at 0° C. On completion of the addition of benzyl-2-bromoacetate, the reaction was stirred at room temperature 17 hours. The organic solvent was removed in vacuo and the residue was taken up in ethyl acetate and washed with saturated Na₂CO₃ solution. The solution was extracted with 1N HCl . The aqueous layer was made basic with Na₂CO₃ and extracted with chloroform. The organic layer was dried (MgSO$_4$) and evaporated. The residue was purified by silica gel flash column chromatography, eluting sequentially with hexane and hexane/ethyl acetate (1:1, v/v) to yield 2.3 g (50.0%) of the title compound as an oil. $^1$H NMR (CDCl$_3$) δ 6 1.25–1.85 (m, 9H); 3.0–3.12 (m, 1H); 3.43 (s, 2H); 5.15 (s, 2H); 7.27–7.42 (m, 5H); $^{13}$C NMR (CDCl$_3$) δ 23.72, 32.71, 49.53, 59.03, 66.24, 128.1, 128.32, 135.42, 172.29.

N-α-Boc-N-cyclopentyglycine

To a stirred solution of N-cyclopentylglycine benzyl ester (2.31 g, 9.9 mmol) and triethyamine (1.66 mL, 11.9 mmol) in DMF (3.0 mL) was added a solution of Di-tert-butyl-dicarbonate (2.16 g, 9.9 mmol) in DMF (3.0 mL). The resulting solution was stirred at room temperature under N$_2$ for 19 hours. DMF was evaporated in vacuo and the resulting oil was dissolved in ethyl acetate (50 mL). Ethyl acetate layer was washed with 10% Na$_2$CO$_3$ solution (2×25 mL), brine (2×30 mL), dried (MgSO$_4$) and the solvent evaporated to give the title compound (3.28 g, 99.0%) as an oil. The compound was used without further purification. $^{13}$C NMR (CDCl$_3$) δ 23.44, 28.13, 29.11, 29.80, 44.86, 56.28, 66.61, 79.96, 128.15, 128.30, 128.46, 135.5, 155.0, 170.48.

N-α-Boc-N-cyclopentylglycine

N-α-Boc-N-cyclopentylglycine benzyl ester (3.28 g 9.9 mmol) was dissolved in deoxygenated ethanol (30 ml) with 10% palladium on carbon (0.33 g). The reaction mixture was agitated under hydrogen (30 P.S.I.) in a Parr hydrogenator for 17 hours. It was filtered through a celite pad and ethanol was evaporated. The resulting residue was dissolved in ethyl acetate and the ethyl acetate layer was washed with cold IN HCl (100 mL), brine (2×100 mL), dried (MgSO$_4$) and evaporated in vacuo. The resulting compound was recrystallized from ethyl acetate/hexane to yield 1.09 g (47.0%) of the title compound as a colorless solid. Anal. (C$_{12}$H$_{21}$NO$_4$) C, H, N; C: calcd., 59.24; found 58.94, H: calcd., 8.70; found, 8.69.; N: calcd., 5.76; found, 6.00. $^1$H NMR (CDCl$_3$) δ 1.2–1.72 (m, 15H); 1.76–1.96 (m, 2H); 3.64–4.0 (br s, 2H); 4.1–4.6 (m, 1H); 10.36 (br s, 1H).

Boc-Ng-p-Tosyl-L-arginine PAM resin (1.52 g, Bachem, 0.5 meq) was charged in a vessel designed for manual solid phase peptide synthesis. The peptide was coupled sequentially and cleaved from the resin using the procedures previously described. Four equivalents of preactivated amino acids were used in the couplings. HF deprotection provided 428 mg of crude material. HPLC purification of 100 mg of the crude material (10–65% CH$_3$CN, 0.1% TFA, gradient over 55 minutes, 20 mL/min) provided 22.3 mg of compound 8 as a white lyophilate. HPLC: R.t.=28.7 minutes (5–70% CH$_3$CN, 0.1% TFA over 65 minutes, C18 5μ, analytical column). LD-MS: Calc. 1278.6 Found 1279.6 (M+1). AAA: Arg 2.93 (3), Hyp 0.96 (1), Pro 1.01 (1), Gly 1.04 (1), Thi*, Ser 0.90 (1), Tic*, NCpg*. Correct sequence analysis was obtained.

EXAMPLE IX

Synthesis of Compound 9

D-Arg-Arg-Pro-Hyp-Gly-Thi-Ser-D-Phe-NChg-Arg

Boc-Ng-p-Tosyl-L-arginine PAM resin (1.52 g, Bachem, 0.5 meq) was charged in a vessel designed for manual solid phase peptide synthesis. The peptide was coupled sequentially and cleaved from the resin using the procedures previously described. Four equivalents of preactivated amino acids were used in the couplings. HF deprotection provided 586.7 mg of crude material. HPLC purification of 100 mg of the crude material (10–65% CH$_3$CN, 0.1% TFA, gradient over 55 minutes, 20 mL/min) provided 72.8 mg of compound 9. HPLC: R.t.=30.5 minutes (5–70% CH$_3$CN, 0.1% TFA over 65 minutes, C18 5μ, analytical column). LD-MS: Calc. 1281.5 Found 1281.5 (M+H). AAA: Arg 3.11 (3), Hyp 0.91 (1), Pro 0.95 (1), Gly 1.00 (1), Thi*, Ser 1.06 (1), Phe 0.97 (1), NChg*.

EXAMPLE X

Compound 10

D-Arg-Arg-Pro-Hyp-Gly-Thi-Ser-D-Cpg-NChg-Arg

N-α-Boc-Cyclopentylglycine

D-Cyclopentylglycine was synthesized by the method of Dunn (Hill, J. T. and Dunn, F. W., *J. Org. Chem.* 30 1321 (1965)). D-cyclopentylglycine (3.93 g, 27.5 mmol) and sodium hydroxide (27.5 mL, 1M solution) were added to a mixture of 150 mL of dioxane and 75 mL water. The solution was chilled to 0° C. and di-tert-butyl dicarbonate (6.60 g, 30.2 mmol) was added. The reaction mixture warmed to room temperature and stirred approximately 15 hours. Volatiles were removed in vacuo and the residue was taken up in water and basified, using 5% NaOH to pH 9. The aqueous layer was extracted three times with ethyl acetate, and the combined extracts were washed with brine, dried over anhydrous sodium sulfate and concentrated in vacuo to yield 5.44 g (81.5%) of the title compound as a glass. $^1$H NMR (CDCl$_3$) δ 1.15–1.9 (m, 8H) 1.45 (s, 9H); 2.25 (m, 1H); 3.99 (dd, 0.32H) 4.25 (dd, 0.68H); 5.01 (d, 7.0 Hz, 0.68H); 6.27 (d, 7.0 Hz, 0.32H), NH and α-H yield two signals arising from rotamers.

Boc-Ng-p-Tosyl-L-arginine PAM resin (1.52 g, Bachem, 0.5 meq) was charged in a vessel designed for manual solid phase peptide synthesis. The peptide was coupled sequentially and cleaved from the resin using the procedures previously described. Four equivalents of preactivated amino acids were used in the couplings. HF deprotection provided 349 mg of crude material. HPLC purification of 100 mg of the crude material (10–65% CH$_3$CN 0.1% TFA, gradient over 55 minutes, 20 mL/min) provided 30.2 mg of compound 10. HPLC: R.t.=29.2 minutes (5–70% CH$_3$CN, 0.1% TFA over 65 minutes, C18 5μ, analytical column) LD-MS: Calc. 1258.9, Found 1258.9 (M+H). AAA: Arg 3.13 (3), Hyp 0.92 (1), Pro 0.96 (1), Gly 0.98 (1) , Thi*, Set 1.02 (1), Cpg*, NChg*.

EXAMPLE XI

Synthesis of Compound 11

D-Arg-Arg-Pro-Hyp-Gly-Thi-Ser-NPeg-Oic-Arg

N-Phenethylglycine benzyl ester hydrochloride

A solution of benzyl-2-bromoacetate (3.3 ml, 20.0 mmol) in CH$_2$Cl$_2$ (30 ml) was added drop-wise to a solution of phenethylamine (12.6 ml, 100 mmol) in CH$_2$Cl$_2$ (30 ml) stirring at 0° C. After warming to room temperature the reaction was stirred for 24 hours, then filtered and the solvent evaporated in vacuo. The resulting residue was dissolved in ethyl acetate, and washed with brine and dried over sodium sulfate. The ethyl acetate was evaporated in vacuo. The crude material was purified using silica gel flash column chromatography eluting sequentially with hexane and ethyl acetate-hexane (9:1, v/v). The fraction containing the product had traces of benzyl-2-bromoacetate as an impurity. This portion was redissolved in CHCl$_3$ and washed with 1N HCl. The chloroform layer was dried and the HCl salt was precipitated with petroleum ether. Yield 2.3 g colorless solid. $^1$H NMR (CDCl$_3$) δ 1.95 (br s, 1H), 2.73–2.9 (m, 3H), 3.44 (s, 2H), 5.12 (s, 2H), 7.13–7.36 (m, 10H). $^{13}$C NMR (CDCl$_3$) δ 36.17, 50.46, 50.63, 66.32, 26.06, 128.18, 128.3, 128.4, 128.50, 135.4, 139.4, 171.88.

N-α-Boc-N-phenethylglycine benzyl ester

To a stirred solution of N-phenethylglycine benzyl ester (2.30 g, 8.54 mmol,) and triethyamine (1.31 ml, 9.4 mmol) in DMF (3.0 ml) was added a solution of di-tert-butyl dicarbonate (1.87 g, 8.54 mmol) in DMF (3.0 ml). The resulting solution was stirred at room temperature under N$_2$ for 22 hours. DMF was evaporated in vacuo and the resulting oil was dissolved in ethyl acetate (50 ml). The ethyl acetate layer was washed with 10% Na$_2$CO$_3$ solution (2×25 ml), brine (2×30 ml), dried (MgSO$_4$) and the solvent evaporated to give 3.13 g (98.0%) of the title compound as an oil. $^1$H-NMR (CDCl$_3$) δ 1.37, 1.44 (rotamers, 9H); 2.75–2.9 (m, 2H); 3.33–3.55 (m, 2H); 3.8, 3.92 (rotamers, 2H); 5.15 (s, 2H), 7.1–7.4 (m, 10H); $^{13}$C NMR (CDCl$_3$) δ 28.09, 28.20, 34.64, 35.02, 49.16, 50.07, 50.39, 66.62, 66.68, 80.12, 126.18, 126.26, 128.14, 128.21, 128.31, 128.38, 128.43, 128.73, 135.41, 138.95, 138.99, 154.85, 155.49, 169.84, 169.89.

N-α-Boc-N-phenethylglycine

N-α-Boc-N-phenethylglycine benzyl ester (3.13 g, 8.47 mmol) was dissolved in ethanol (50 ml) and 10% Pd/C (0.3 g) was suspended in that solution after careful degassing with nitrogen. The reaction mixture was agitated under hydrogen atmosphere (~40 P.S.I.) in a Parr hydrogenator for 18 hours. The mixture was then filtered through a celite pad and the ethanol was evaporated. The resulting residue was dissolved in ethyl acetate and washed with cold 1N HCl (100 ml), brine (2×100 ml), dried (MgSO$_4$) and evaporated in vacuo to yield 2.16 g (88.2%) of the title compound as a colorless solid. $^1$H NMR (CDCl$_3$) δ 1.45 (s 9H); 2.8–2.92 (m, 2H), 3.44–3.6 (m, 2H), 3.8, 3.92 (rotamers, 2H), 7.12–7.36 (m, 5H), 11.32 (br s, 1H); $^{13}$C NMR (CDCl$_3$) δ 34.65, 35.01, 49.15, 49.69, 50.37, 50.55, 80.64, 80.77, 126.32, 126.42, 128.5, 128.56, 128.80, 138.79, 138.93, 155.97, 175.32, 176.02.

Boc-Ng-p-Tosyl-L-arginine PAM resin (1.52 g, Bachem, 0.5 meq) prederivatized with Na-Boc-Ng-p-Tosyl-L-arginine was charged in a vessel designed for manual solid phase peptide synthesis. The peptide was coupled sequentially and cleaved from the resin using the procedures previously described. Four equivalents of preactivated amino acids were used in the couplings. HF deprotection provided 487 mg of crude material. HPLC purification of 100 mg of the crude material (10–70% CH$_3$CN, 0.1% TFA, gradient over 60 minutes, 20 mL/min) provided 23.0 mg of compound 11 as a colorless lyophilate. HPLC: R.t.=32.8 minutes (5–70% CH$_3$CN, 0.1% TFA over 65 minutes, C18 5µ, analytical column). LD-MS: Calc 1305, Found 1305. AAA: Arg 3.16 (3), Hyp 0.91 (1), Pro 0.94 (1), Gly 1.00 (1), Thi*, Ser 1.00 (1), Oic*, NPeg.

EXAMPLE XII

Synthesis of Compound 12

D-Arg-Arg-pro-Hyp-Gly-Thi-Ser-D-Tic-NMch-Arg

N-Cyclohexanemethylglycine benzyl ester

Starting with 2.38 g (10 mmol) benzyl 2-bromoacetate and 5.66 g of cyclohexanemethylamine, the compound was synthesized using the same procedure as that for N-phenethylglycine benzyl ester. The product was purified by precipitation of the hydrochloride salt. The hydrochloride salt was then dissolved in CHCl$_3$ and CHCl$_3$ layer was washed with Na$_2$CO$_3$ (10%) to isolate 1.3 g (52.0%) of the title compound as an oil. $^{13}$C NMR (CDCl$_3$) of HCl salt. δ 25.21, 25.27, 25.72, 25.83, 30.43, 30.68, 30.84, 34.64, 37.58, 46.25, 47.46, 54.17, 68.11, 128.63, 128.70, 128.81, 134.243, 165.63.

N-α-Boc-N-cyclohexanemethyl glycine benzyl ester

The procedure is the same as that for Boc-N-phenethylglycine benzyl ester, starting with 1.39 g of N-cyclohexanemethylglycine benzyl ester. Yield 1.8 g (94.0%) as an oil.

N-e-Boc-N-Cyclohexanemethylglycine

The procedure is the same as that for Boc-N-phenethylglycine starting with 1.80 g of N-α-Boc-N-Cyclohexanemethyl glycine benzyl ester. Yield 1.28 g (95.0%) isolated as a colorless solid. $^1$HNMR (CDCl$_3$) δ 0.84–1.8 (m, 20H); 3.04–3.2 (m, 2H); 3.9–4.04 (rotamers, 2H); 11.44 (br s, 1H); $^{13}$C NMR (CDCl$_3$) δ 25.67, 25.78, 26.25, 26.36, 28.13, 28.19, 28.24, 30.59, 30.63, 30.72, 36.85, 37.08, 37.69, 45.53, 49.08, 49.69, 54.47, 54.62, 80.17, 80.37, 155.46, 156.37, 174.68, 175.06.

Boc-Ng-p-Tosyl-L-arginine PAM resin (1.52 g, Bachem, 0.5 meq) was charged in a vessel designed for manual solid phase peptide synthesis. The peptide was coupled sequentially and cleaved from the resin using the procedures previously described. Four equivalents of preactivated amino acids were used in the couplings. HF deprotection provided 480 mg of crude material. HPLC purification (5–70% CH$_3$CN, 0.1% TFA, gradient over 60 minutes, minutes, 20 mL/min) provided a total of 191 mg of compound 12 as a colorless lyophilate. HPLC: R.t.=33.7 minutes (5–70% CH$_3$CN, 0.1% TFA over 65 minutes, C18 5µ, analytical column). LD-MS: Calc. 1307, Found 1308 (M+H). AAA: Arg 3.16 (3), Hyp 0.91 (1), Pro 0.94 (1), Gly 1.00 (1), Thi*, Ser 0.99 (1), Tic*, NMch*.

EXAMPLE XIII

Compound 13

δ-Gpa-Arg-pro-Hyp-Gly-Thi-Ser-D-Tic-NChg-Arg

Boc-Ng-p-Tosyl-L-arginine Merrifield resin (4.20 g, Bachem RBoc20, 0.48 meq/g) was charged in a vessel designed for manual solid phase peptide synthesis. The peptide was coupled sequentially to form a tetrapeptide (Ser-(OBn) coupling), then the process was transferred to a CS-BIO automated peptide synthesizer for the addition of Gly, Hyp, Pro, and Arg. A portion of this peptidyl resin (0.53 gram) was removed from the reaction vessel. The resin sample was deprotected with TFA as described above and N-(Boc)-d-aminovaleric acid was coupled using the procedure described above for HOBt/diimide activation. This residue was deprotected with trifluoroacetic acid as described previously and neutralized by washing sequentially with dichloromethane, 10% diisopropylethylamine in dichloromethane, dichloromethane, and finally with DMF. The resin was heated with a mixture of 0.566 g of 1H-pyrazole-1-carboxamidine (Bernatowicz, M. S. et al., J. Org. Chem. 57 2497 (1992)) and 0.76 mL of diisopropylethylamine in 20 mL of DMF at 47° C. for 2.25 hours. The resin was washed with dichloromethane and dimethylformamide and the reaction with 1H-pyrazole-1-carboxamidine was repeated two additional times. The resin was washed sequentially with dichloromethane, methanol, then dichloromethane and dried in vacuo. HF deprotection provided 80 mg of compound 13 as a colorless lyophilate. HPLC: R.t.=22.6 minutes (5–55% CH$_3$CN, 0.1% TFA over 50 minutes, C18 5µ, analytical column). LD-MS: Calc. 1278 (M+H), Found 1278.7 (M+H).

EXAMPLE XIV

Compound 14

δ-Gpa-Pro-Hyp-Gly-Thi-Ser-D-Tic-NChg-Arg

Boc-Ng-p-Tosyl-L-arginine Merrifield resin (4.20 g, Bachem RBoc20, 0.48 meq/g) was charged in a vessel designed for manual solid phase peptide synthesis. The peptide was coupled sequentially to form a tetrapeptide (Ser-(OBn) coupling), then the process was transferred to a CS-BIO automated peptide synthesizer for the addition of Gly, Hyp, and Pro. A portion of this peptidyl resin (0.260 gram) was removed from the reaction vessel. The resin was deprotected with TFA as described above and N-(Boc)-d-aminovaleric acid was coupled using the procedure described above for HOBt/diimide activation. This residue was deprotected with trifluoracetic acid as described previously and neutralized by washing sequentially with dichloromethane, 10% diisopropylethylamine in dichloromethane, dichloromethane, and finally with DMF. The resin was heated with a mixture of 0.405 g of 1H-pyrazole-1-carboxamidine (Bernatowicz, M. S. et al., *J. Org. Chem.* 14 48–58 (1959)) and 0.545 mL of diisopropylethylamine in 14.5 mL DMF at 47° C. for 2.25 hours. The resin was washed with dichloromethane and dimethylformamide and the reaction with 1H-pyrazole-1-carboxamidine was repeated. The resin was washed sequentially with dichloromethane, methanol, then dichloromethane and dried in vacuo. HF deprotection provided 30 mg of compound 14 as a colorless lyophilate. HPLC: R.t.=22.3 minutes (5–55% $CH_3CN$, 0.1% TFA over 50 minutes, C18 5µ, analytical column). LD-MS: Calc. 1123 (M+H), Found 1123 (M+H).

EXAMPLE XV

Compound 15

D-Arg-Arg-Pro-Hyp-Gly-Thi-Ser-D-Tic-NPhg-Arg

Fmoc-D-Tic Acid Chloride

One equivalent of the Fmoc-D-Tic was dissolved in $CH_2Cl_2$ (0.3M) and placed in a flask equipped with a stir bar and reflux condenser. Thionyl chloride (10 equivalents) was added with stirring and the mixture refluxed, under nitrogen, for 2 hours. The reaction mixture was concentrated by rotary evaporation and the residue was diluted with $CH_2Cl_2$ and concentrated again to remove excess thionyl chloride. This was repeated twice and the resulting acid chloride was triturated with hexane (or alternatively recrystallized from $CH_2Cl_2$/hexane) until a fine powder was obtained. Used without further purification.

Fmoc-D-Tic-N-Phenylglycine

N-Phenylglycine (1.2 equivalents) was suspended in dry THF (0.5M) in a flask and three equivalents of diisopropylethylamine were added. The flask was placed in an ice-water bath and stirred for 15 minutes under nitrogen. One equivalent of Fmoc-D-Tic acid chloride was dissolved in dry THF (0.15M) and added slowly to the cooled flask. A precipitate began to form immediately and the reaction was allowed to warm to room temperature and stirred for 2 hours. Once the reaction was completed the solvent was removed by rotary evaporation, the residue taken up in ethyl acetate and washed with 5% $KHSO_4$, $H_2O$ and brine. Drying with $Na_2SO_4$, rotary evaporation and placement under high vacuum yielded a white foam. The dipeptide was analyzed by HPLC ($C_{18}$ RP column, 4.6×250 mm, 1 mL/min flow rate, 30 minute gradient from 30–100% $CH_3CN/H_2O$ containing 0.1% TFA, detection at 254 nm) for purity and was utilized without further clean-up.

Attachment of Fmoc-D-Tic-NPhg-OH to Arg-OHMP Resin

The coupling of the Fmoc-D-Tic-NPhg-OH dipeptide (~0.785 mmol) to the peptidyl resin (0.25 mmol) was carried out using Bop-Cl under conditions as described above for the couplings of N-protected amino acids to hindered N-substituted amino acids.

Peptide Synthesis: The Fmoc-D-Tic-NPhg-Arg-OHMP resin was N-deprotected by reaction with 20% piperidine in DMF (2×30 minutes). The resin was then washed, sequentially, three times with DMF, twice with dichloromethane, twice with methanol, and twice with dichloromethane. Fmoc-Serine-(O-t-Bu)-OH was coupled using the Bop-Cl procedure as described above. The resin was then transferred to an ABI model 431 automated peptide synthesizer and the additional residues were added using standard Fmoc/HBTU coupling procedures (ABI 431 Fmoc Procedure, *Applied Biosystems Model 431A Peptide Synthesizer User's Manual*, Version 2.0, January 1992). The resin was then washed several times with dichloromethane and dried in a stream of anhydrous nitrogen. The resin was then treated with 10 mL trifluoroacetic acid containing 0.5 mL of thioanisole and 0.25 mL of ethanedithiol. The reaction bubbled for 3 hours at room temperature. The mixture was filtered, and the resin was washed with ~1 mL of trifluoroacetic acid. The combined filtrates were concentrated in vacuo and the residue was treated with anhydrous diethyl ether and allowed to stand at ice-bath temperature for fifteen minutes. The precipitate was then collected by filtration and was washed well with cold, anhydrous, diethyl ether, and dried in vacuo, resulting in 205 mg of colorless powder. HPLC purification of a small portion of this material (0–35% $CH_3CN$, 0.1% TFA, gradient over 50 minutes, 10 mL/min) provided 10 mg of compound 15 as a colorless lyophilate. HPLC: R.t.=20.9 minutes (5–55% $CH_3CN$, 0.1% TFA over 50 minutes, C18 5µ, column). LD-MS: Calc. 1287.5 (M+H), Found 1287.5 (M+H). Correct amino analysis data was obtained.

EXAMPLE XVI

Compound 16

D-Arg-Arg-Pro-Hyp-Gly-Thi-Ser-D-Phe-NPhg-Arg

The dipeptide Fmoc-D-Phe-NPhg-OH was prepared according to the method used to prepare Fmoc-D-Tic-NPhg-OH in compound 15. The dipeptide Fmoc-D-Phe-NPhg-OH (~0.5 mmol) was coupled to Arg-HMP resin (0.25 mmol) using the procedures as described in compound 15. The peptide was synthesized, and cleaved from the resin as described in compound 15 to provide 260 mg of crude peptide. HPLC purification of 75 mg of this material (5–50% $CH_3CN$, 0.1% TFA, gradient over 60 minutes, 10 mL/min) provided 18.9 mg of compound 16 as a colorless lyophilate. HPLC: R.t.=21.9 minutes (5–55% $CH_3CN$, 0.1% TFA over 50 minutes, C18 5µ, analytical column). LD-MS: Calc. 1275 (M+H), 1298 (M+Na); Found 1274 (M+H), 1298 (M+Na).

EXAMPLE XVII

Compound 17

D-Arg-Arg-Hyp-Hyp-Gly-Thi-Ser-D-Tic-NChg-Arg

Boc-Ng-p-Tosyl-L-arginine Merrifield resin (4.2 g, Bachem, RBOC20, 0.48 meq/g) was charged in a vessel designed for manual solid phase peptide synthesis. The peptide was coupled sequentially and cleaved from the resin using the procedures previously described. Four equivalents of preactivated amino acids were used in the couplings. HF deprotection provided 1.05 g of crude material. HPLC purification of a small portion of this material (0–65% $CH_3CN$, 0.1% TFA, gradient over 50 minutes, 10 mL/min) provided compound 17 as a colorless lyophilate. Correct amino acid and peptide sequence data were obtained.

EXAMPLE XVIII

Biological Data

The most preferred compounds of the present invention are antagonists of bradykinin and as such have wide utility therapeutic intervention in disease states or pathophysiologic conditions where the action of bradykinin is implicated. The following protocols describe assays used herein for determining bradykinin antagonist activity in vitro and in vivo and assays for characterizing the selectivity and in vivo stability of various compounds according to the invention.

In vitro $B_2$ Antagonist Activity Measurements

The standard rat uterus pA2 assay was conducted as follows:

Female Sprague-Dawley rats (200–250 g) were pretreated with stilbesterol (100 μg/kg) and killed 18 hours later by a blow on the head and exsanguinated. Uterine horns were removed, placed under a 1 g resting tension in 4 mL tissue baths containing De Jalon's solution at 31° C. and aerated. Concentration-effect curves were constructed for bradykinin in the absence and presence of antagonist (preincubated for 15 minutes). Antagonist potency was calculated according to the method of Arunlakshana and Schild (Arunlakshana, O., Schild, H. O., Br. J. Pharmacology 14 48–58 (1959)). Following exposure to the highest concentration of antagonist (usually $10^{-5}$ molar) each tissue was washed at 10 minute intervals for 40 minutes, after which time a concentration-effect curve was again constructed for bradykinin. The pD2 (-log[molar concentration producing 50% of the maximum original response to bradykinin]) for bradykinin at this time was calculated and compared to the $pD_2$ of the initial control concentration-effect curve for bradykinin. The difference in $pD_2$ values compared to concurrent control reflected the "percentage recovery" of agonist response.

In vitro $B_1$ Antagonist Activity Measurements

Female New Zealand White rabbits were killed by overdose of pentobarbital (80 mg/kg i.v.) and the thoracic aorta removed. Spiral strips were mounted under 2 g resting tension in 5 mL tissue baths containing Krebs solution (118.3 mM NaCl, 4.7 mM KCl, 2.5 mM $CaCl_2$, 1.2 mM $MgSO_4$ 1.2 mM $KH_2PO_4$, 25 mM $NaHCO_3$, 25 mM glucose, and 2.8 μM indomethacin) and aerated with 95% $O_2$/5% $CO_2$. Two concentration-effect curves for des-$Arg^9$-bradykinin were constructed at 1 and 3 hours. At five hours des-$Arg^9$-bradykinin was added to the bath to a final concentration of $10^{31}$ $^7$M. This produced stable, sustained and prolonged contractions of up to 45 minutes. The $IC_{50}$ or concentration producing 50% reversal of the contraction was then calculated from the resulting tracings. The results obtained are shown in Table 1.

Stability Studies

Plasma samples were prepared by collection of whole blood from healthy male and female human volunteers or guinea pigs. Samples were collected into culture tubes containing sodium heparin, and were then spun at 4° C. at 2000 rpm for ten minutes. Supernatant fractions were removed by aspiration and stored in vials at −20° C. Rat or porcine lung and kidney cortical membranes were prepared using differential centrifugation as described by Skidgel (Booth, A. G. et al., Biochemical Journal 142, 575–581 (1974)) for lung or by Booth (Erdos, E. G. et al., Biochemical Pharmacology 33 3471–3478 (1984)) for kidney. Membrane preparations were stored at −20° C. Bradykinin antagonists were diluted to 1 mM concentration in PBS (0.0132M phosphate, 0.1454M NaCl, pH 7.2). Ten microliters of this working solution were delivered into a series of Eppendorf tubes, followed by human or guinea pig plasma (90 μL) or PBS as a control blank, and incubated for various time periods. At each time point the reaction was quenched with the addition of 100 μL 1N HCl in either acetonitrile or ethanol. Samples were allowed to stand approximately fifteen minutes and were then spun at 14,000 rpm for 10 minutes. Supernatant fractions were removed, filtered through 0.22 μM filters (Millipore) and analyzed by HPLC (C18, 12–80% acetonitrile in water, both containing 0.1% trifluoroacetic acid, monitoring at 214 nm.

Porcine kidney lung preparations were diluted 1:10 with PBS; rat kidney preparations were diluted 1:100 with PBS; porcine lung preparations were diluted 1:1 in PBS. The bradykinin antagonist solutions (10 μL) were added to a series of Eppendorf tubes, followed by the respective diluted membrane preparations (90 μL). At various time points the reactions were quenched by the addition of 100 μL of ethanol, centrifuged and analyzed by HPLC as described above. The half-life for the disappearance of the HPLC peak was determined using the computer program ENZFIT (Elsevier). Stability data are given in Table 2.

TABLE 1

In Vitro Bradykinin Antagonist Activity in Functional Tissue Assays

| Compound | $B_2$ $pA_2$ (Rat Uterus) | n | % Recovery | $B_1$ (Rabbit Aorta) | n |
|---|---|---|---|---|---|
| 1 | 5.67 ± 0.17 | 3 | 32 | 6.41 ± 0.25 | 3 |
| 2 | 6.76 ± 0.71 | 3 | 0 | 5.79 ± 0.065 | |
| 3 | 6.41 ± 0.49 | 3 | 100 | <5 | 4 |
| 4 | Agonist | | | <5 | 4 |
| 5 | 9.5 ± 0.05 | 10 | 71 | <5 | 3 |
| 6 | 7.3 ± 0.03 | 3 | 93 | <5 | 2 |
| 7 | Agonist | | | <5 | 2 |
| 8 | 8.50 ± 0.09 | 3 | 56 | <5 | 4 |
| 9 | 7.73 ± 0.09 | 3 | 87 | 5.52 | 4 |
| 10 | 5.85 ± 0.09 | 3 | 75 | 5.34 | 4 |
| 11 | Agonist | | | <5 | 4 |
| 12 | Agonist | | | <5 | |
| 13 | 9.09 ± 0.25 | 10 | 66 | | |
| 14 | 7.65 ± 0.25 | 6 | 81 | | |
| 15 | 8.88 ± 0.12 | 6 | 54 | | |
| 16 | 7.68 ± 0.09 | 6 | 60 | | |
| 17 | 8.48 ± 0.38 | 5 | 60 | | |
| CP-0589* | 6.9 ± 0.89 | 3 | 57 | Not tested | |
| CP-0601* | 7.0 ± 0.20 | 3 | 75 | Not tested | |
| HOE-140 | 10.3 | 7 | 41 | Inactive | |

*CP-0589 D—Arg—Arg—Pro—Hyp—Thi—Gly—Ser—D—Tic—Oic—Arg
*CP-0601 D—Arg—Arg—Pro—Hyp—Gly—Gly—Ser—D—Tic—Oic—Arg
Both compounds were synthesized by conventional methods of solid phase peptide synthesis as described for compounds 1–12.

Antagonist Binding to Guinea Pig ileum

Ilea were collected from cervically dislocated male albino, Hartley-strain guinea pigs. The ilea were flushed with ice cold saline, everted, and wiped with cotton gauze. The tissue was then frozen and stored at −70° C. Upon use, grams of ilea were thawed on ice, finely chopped with a tissue chopper and then added to 10 volumes (350 mL) of TES homogenization buffer (25 mM, pH 6.8) containing a protein inhibitor cocktail (1 mM 1, 10-phenanthroline, 5 µg/mL soybean trypsin inhibitor, 100 ug/mL bacitracin, 1 mM benzamidine, and 100 µM phenylmethylsulfonyl fluoride. This mixture was homogenized in a Brinkman PT-20 Polytron (setting 7, 4×20 second intervals) and subjected to differential centrifugation (1000×g, 4° C., 10 minutes). The pellet was discarded and the solution brought back up to volume using fresh homogenization buffer and then centrifuged for 15 minutes at 43,000×g, 4° C. The pellet was carefully resuspended in homogenization buffer and centrifuged as before. The supernatant was again discarded and the pellet was suspended in TES buffer (25 mM, pH 6.8) and centrifuged (43,000 g, 15 minutes). The final pellet was resuspended in 5 volumes (165 mL) of TES buffer yielding approximately 2.0 mg of protein per mL and stored at −70° C. until used. Incubations were carried out in a total volume of 0.315 mL, consisting of 20 uL tritium labeled bradykinin solution (0.3 nM) 20 uL non-specific control, drug or vehicle, 150 µL assay buffer (25 mM TES, pH 6.8 1 mM 1,10 phenanthroline, 1 mM DTT, 2 µM captopril, 140 µg/mL bacitracin, 100 µM thiorphan, and 0.1% bovine serum albumin, and 125 µL diluted membrane (diluted 1:4 for final concentration of 0.2 mg/mL) added last to initiate binding. The assay was carried out in polypropylene tubes, and samples were allowed to incubate at 24° C. for 45 minutes. The mixtures were then rapidly filtered through Whatman GF/B glass fiber filters pretreated (>2 hours) with 0.1% aqueous polyethylenimine. The filters and tubes were then washed with eight 1.0 mL portions of ice cold wash buffer containing 10 mM Tris (pH 7.5), 100 mM NaCl, and 0.02% bovine serum albumin. Radioactivity was determined by liquid scintillation counting.

Data for compound 5, which is also designated as CP-0597, and standards are given in Table 2.

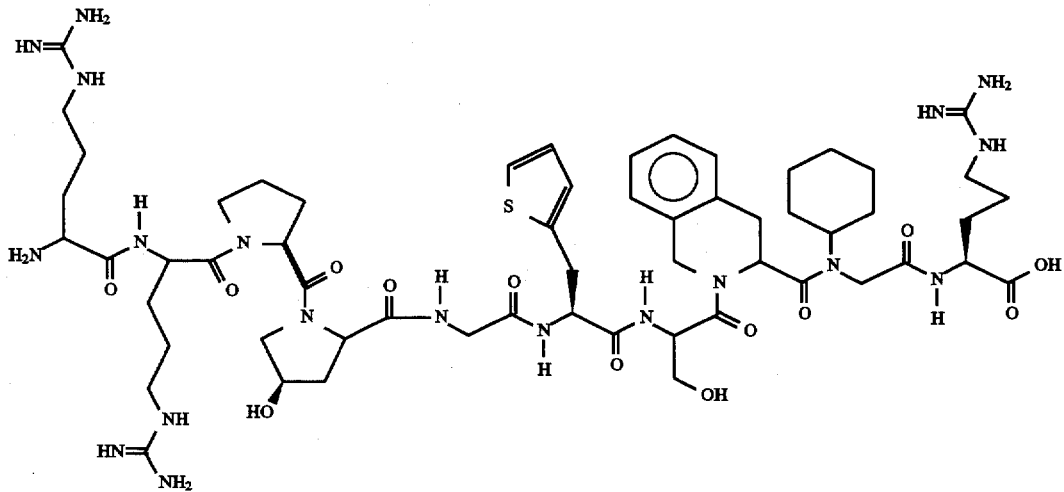

CP-0597 (Example 5)

TABLE 2

In Vitro Data Summary

|  | HOE-140 | CP-0597 | CP-127 | Bradykinin |
|---|---|---|---|---|
| B2 |  |  |  |  |
| pA2 |  |  |  |  |
| (rat uterus) | 10.3 | 9.5 | 8.5 | — |
| B2 binding | 1.4 pM | 1.3 pM | 4.8 nM | 30.1 pM |
| (G.P.I.) |  |  |  |  |
| Half-life Data |  |  |  |  |
| Human Plasma | >6 hr. | >6 hr. | 2.75 hr. | 0.45 hr. |
| Rat Kidney | N.D. | >6 hr. | 0.66 hr. | 0.13 hr. |
| Porcine* Kidney | N.D. | >6 hr. | >6 hr. | 0.05 hr. |
| Porcine Lung | N.D. | >6 hr. | 0.15 hr | 0.05 hr. |

*NPC17761 1.17 hour
*NPC17731 4.34 hour

CP-127 is a dimer disclosed in Example 1 of application Ser. No. 07/859,582 of the formula:

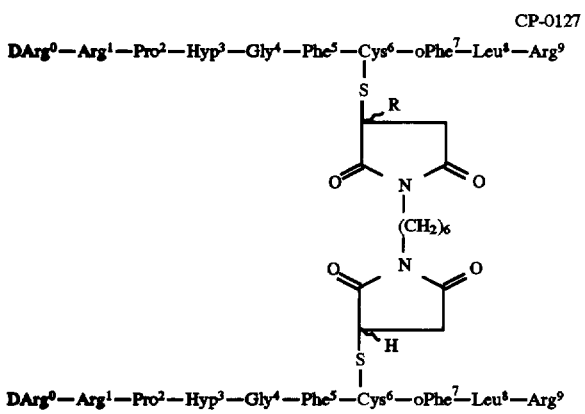

CP-0127

DArg⁰—Arg¹—Pro²—Hyp³—Gly⁴—Phe⁵—Cys⁶—oPhe⁷—Leu⁸—Arg⁹

DArg⁰—Arg¹—Pro²—Hyp³—Gly⁴—Phe⁵—Cys⁶—oPhe⁷—Leu⁸—Arg⁹

The compound is itself a highly active bradykinin antagonist.

In Vivo Biological Data
Rabbit Blood Pressure

Male New Zealand White rabbits were anesthetized with pentobarbital and femoral arteries were cannulated for the recording of blood pressure. Cannulae were placed in the femoral veins for the bolus injection or continuous infusion of compounds. The femoral arterial catheters were connected to a Gould pressure transducer and blood pressure was recorded and displayed on a Grass polygraph recorder. Following an equilibration period the specific experimental procedure was started.

$BK_2$ $ED_{50}$—following the establishment of a stable baseline blood pressure, the animals were administered bolus injections of Bradykinin that produced approximately a 15–25% decrease in blood pressure (0.2 and 0.4 nmol, i.v.). Bradykinin was tested in the absence and then in the presence of various doses of CP-597 (compound 5) (0.01, 0.03, and 0.10 µg/kg/min i.v.) for the determination of the $ED_{50}$ (i.e. the dose of CP-0597 reducing the maximum-response to Bradykinin by 50%). In this system the $ED_{50}$ was found to be 0.051±0.006 µg/kg/min (29.2 pmol/kg/min).

$BK_1$ $ED_{50}$—Rabbits were injected with lipopolysaccharide (LPS) from E. Coli, (10 µg/animal) intravenously 12–18 hours before the experiment. Preadministration of endotoxin results in the upregulation of $BK_1$ receptors in the vascular system and allows the evaluation of $BK_1$ antagonist activity. Stimulation of both pre-existing $BK_2$ and induced $BK_1$, receptors produces hypotension. After blood pressure equilibration the animals were administered bolus injections of Bradykinin (0.2 and 0.4 nmol) and des-Arg⁹Bradykinin (4.0 and 8.0 nmol). Both agonists were tested in the absence and then in the presence of increasing doses of CP-0597 (1, 3, and 10 µg/kg/min). The $ED_{50}$ for $BK_1$ activity in this system was found to be 2.9±0.92 µg/kg/min (1.7 nmol/kg/min). HOE140 was inactive at doses up to 10 ug/Kg/min.

Selectivity Of Intravenous CP-0597

Following equilibration of blood pressure responses produced to acetylcholine (20 nmol), norepinephrine (20 nmol), substance p (20 pmol), angiotensin (100 pmol), angiotensin II (2 pmol), and bradykinin (200 pmol), each vasoactive agent was then retested after the administration of CP-0597 (0.1 µg/kg/min i.v.) and compared to pre-antagonist responses. In this study the response to Bradykinin was antagonized whereas those to the other vasoactive agents were unaffected compared to controls.

Duration Of Action Of Intravenously Infused CP-0597

CP-0597 (0.1 µg/kg/min) was intravenously infused for the above mentioned selectivity experiments. After the selectivity experiment was complete, the infusion of CP-0597 was stopped and the response to Bradykinin (0.2 and 0.4 nmol) was tested at 5 min intervals for the first 30 min and at 15 min intervals up to one hour. At one hour after the infusion had been stopped there was still 100% inhibition of the response to Bradykinin.

Rat Blood Pressure

Male Sprague-Dawley rats were anesthetized with pentobarbital and femoral arteries were cannulated for the recording of blood pressure. Both femoral veins in each animal were cannulated for the administration of test compounds. The femoral arterial catheters were connected to a Gould pressure transducer and blood pressure was recorded and displayed on a Grass polygraph recorder. Following an equilibration period the specific experimental procedure was started.

Selectivity Of Subcutaneous CP-0597

Following equilibration of blood pressure, responses were produced to acetylcholine (20 nmol), norepinephrine (1 nmol), substance p (2 pmol), angiotensin (20 pmol), angiotensin II (2 pmol), and bradykinin (20 pmol i.a.). Animals were then treated with CP-0597 (1.0 mg/kg s.c.). Thirty minutes after the s.c. injection each vasoactive agent was retested and compared to pre-antagonist responses. In this study the response to Bradykinin was antagonized whereas those to the other vasoactive agents were unaffected compared to controls.

Duration Of Action Of I.V. Bolus Injections OF CP-0597

Following equilibration of blood pressure responses to Bradykinin (10 and 20 pmol i.a.) were produced as control responses. CP-0597 was then administered as an i.v. bolus (either 3, 10 or 30 mg/kg) and the response to Bradykinin retested at 5 minute intervals until the response returned to control levels. At 3 µg/kg the response was ca. 50% inhibited and had returned to control by 30 minutes. At 20% and 30 µg/kg the response was 100% inhibited with a 50% return to control level by 60 minutes and full recovery of response by 90 minutes.

Duration of Action Of Subcutaneous CP-0597

After equilibration of mean arterial blood pressure, animals were challenged with Bradykinin (10 and 20 pmol i.a.) to establish control responses. Animals were then given subcutaneous injections of CP-0597 (1 and 3 mg/kg s.c.). Thirty minutes after injection of CP-0597 and at 30 minute intervals thereafter, animals were retested with Bradykinin until responses had returned to control levels. At 1 mg/kg s.c. the responses were still 100% inhibited at 3 hours post injection. At 3 mg/kg s.c. the responses were still 100% inhibited at 5 hours post injection. In vivo biological data are summarized in Table 3.

TABLE 3

In Vivo Biological Data for Example 5 (CP-0597).

| Experiment | Species | Dose | (n) Results |
|---|---|---|---|
| BK2 ED50 | Rabbit | .01, .03, .10 μg/kg/min | (3) ED50 = .051 μg/kg/min (29.2 pmol/kg/min) |
| BK1 ED50 | Rabbit | 1, 3, 10 μg/kg/min | (4) ED50 = 2.9 μg/kg/min (1.7 nmol/kg/min) |
| Duration of Action (i.v. infusion) | Rabbit | 0.1 μg/kg/min | (3) 100% inhibited at 60 min |
| Selectivity (i.v. infusion) | Rabbit | 0.1 μg/kg/min | (3) BK2 block only |
| Duration of Action (s.c.) | Rat | 1 mg/kg | (2) 100% inhibited at 3 hours |
| Duration of Action (s.c.) | Rat | 3 mg/kg | (3) 100% inhibited at 5 hours |
| Duration of Action (i.v. bolus) | Rat | 3.0 μg/kg/min | (3) 50% inhibition; 100% recovery by 30 min 100% inhibition; 50% |
|  |  | 10 μg/kg/min | (3) recovery by 60 min, 100% recovery by 90 min; 100% inhibition; 50% recovery by |
|  |  | 30 μg/kg/min | (3) 60 min, 100% recovery by 90 min |

Table 1, illustrates that highly potent bradykinin antagonists can be developed which include N-substituted glycine residues at position 8 in the bradykinin sequence. For example, compounds 5, 8, 13, 15, and 17 are highly potent antagonists with potency that suggests a high propensity for efficacious effect as a pharmaceutical agent.

Compounds 4, 7, 11 and 12 are found to be agonists using rat uterus as a functional tissue assay. It will be understood by those skilled in the art that agonists are also of potential value as cardioprotective agents. Further, it is understood by those skilled in the art of development of bradykinin antagonists that compounds that are agonists on one type of tissue may be antagonists on another type of tissue. For example, Stewart has disclosed bradykinin antagonists containing D-Phe in position 7 in the bradykinin sequence. Stewart's antagonists (based on guinea pig ileum data) containing D-Phe in position 6 and position 7 such as NPC-360 were found to be agonists on rat uterus (See, U.S. Pat. No. 4,693,993, and J. Stewart in Bradykinin antagonists; Basic and Clinical Research, p. 60, 991). Indeed, similar phenomenon accompany selected compounds in this disclosure. For example, compound 12 was shown to be an agonist on rat uterus tissue, but showed antagonist activity on guinea pig ileum with an extremely tight binding constant (Ki=0.2 picomolar guinea pig ileum). Compounds with a high degree of tissue selectivity may function as dual action drug agents where antagonist activity may be desirable on one tissue but antagonist activity may be desirable on other tissues. Such considerations especially apply to the development of cardioprotective agents.

The most preferred compounds of this invention contain an aromatic D-amino acid at position 7 and an N-substituted glycine at position 8, where the substituent is moderate sized cycloalkyl or phenyl. These analogs yield BK2 antagonist activity on a number of tissue types. Introduction of a methylene unit between the aromatic or cycloalkyl ring increases the propensity for agonist activity on a number of tissue types. Similarly, N-benzylglycine or ring substituted N-benzylglycine at position 7 produces antagonists of moderate potency, provided a conformationally constrained residue such as Oic is present at position 8. If an additional methylene spacer is added to the glycine N-substitution, the extension in geometry is expected to produce agonists on many tissues of interest. Similarly, if the constrained residue at position 8 is replaced by a non-constrained residue such as Leu, or N-Chg, weak agonist activity is expected on many tissues of interest.

The intrinsic value of selected replacements of N-substituted glycine residues, particularly those at position 8, is that judicious choice of the substituent has a tremendous effect on binding of the compound to the bradykinin receptor, where potent antagonists or very tight binding agonists are produced.

The introduction of N-substituted glycine residues allows the development of highly potent molecules with very good properties for pharmaceutical agents. One of the most important properties conferred by the introduction of N-substituted glycines is stability to enzymatic breakdown. Table 2 illustrates that preferred compounds, with N-substituted glycine residues at position 8, such as compound 5, exhibit extremely potent receptor binding on selected tissues. These analogs are much more potent than bradykinin or drugs such as the bradykinin antagonist CP-127 disclosed in Example 1 of commonly owned U.S. patent application Ser. No. 07/859,582.

More importantly, Table 2 illustrates the remarkable stability of compound 5 to degradation by important enzyme systems. Peptide drugs are rapidly degraded by peptidases. In particular molecules related to bradykinin are rapidly degraded by aminopeptidases, carboxypeptidases (CP), and endopeptidases such as neutral endopeptidase (NEP) and angiotensin converting enzyme (ACE). Human plasma is rich in peptidase activity arising from the actions of carboxypeptidase N, and aminopeptidase M. The preparations described in this disclosure exhibit strong activity from the protease enzymes as described below:

| Pig Kidney | Pig Lung | Rat Kidney | Rat Lung |
|---|---|---|---|
| NEP | ACE | NEP | ACE |
| ACE | CP—M | ACE | NEP |
|  |  | Mcprin | CP—M |
|  |  | Endopeptidase-24, 16 |  |

The stability assays summarized in Table 2 represent in vitro tests. The actual stability of an individual compound in plasma or kidney or lung tissue in a living animal may vary. However, the in vitro assay provides a reproducible method for comparison of many compounds without sacrificing large numbers of animals for in vivo experimentation. Thus, this battery of plasma and tissue preparations allows a very broad screening for stability of peptides towards protease enzyme activity likely to be encountered by a peptide drug. Compound 5 is extremely potent with a half-life of greater than six hours in all of these tests. In comparison, bradykinin exhibits significantly less stability. It also appears that Compound 5 has greater stability than CP-127. Other reference compounds such as NPC17761 and NPC17731, developed by Scios-Nova, containing substituted proline residues at position seven and Oic at position 8, exhibited measurably lower stability in crucial assays.

The data presented in Table 3 confirms the correlation between in vitro and in vivo testing. Compound 5 is exceptionally potent in blocking the action of bradykinin at BK2 receptors in live rabbits (ED50 0.051 ug/kg/min). In addition, compounds 5 exhibits substantial BK1 blocking activity in live rabbits (2.9 ug/kg/min). Both assays are extremely relevant to the hypotensive effect of bradykinin in toxic shock and are of interest in predicting efficacious effect in treatment of SIS/sepsis. Not only is the illustrated compound potent in live animals, the compound also exhibits long duration of action (Rabbits 100% inhibited at 60 minutes, i.v.). Indeed, potencies allowing complete blockage of agonist effect up to 5 hours after a subcutaneous dose (3 mg/Kg, rat) were demonstrated. Such stability from a peptide derived agonist is extremely unusual and demonstrates the propensity for good utility of agonists containing N-substituted glycines as pharmaceutical agents.

Finally, studies were performed using both rabbit and rat blood pressure models to demonstrate that blockage of hypotensive effect was related to blockage of bradykinin receptors. The activity of other vasoactive agents such as acetylcholine, norepinephrine, substance P, angiotensin, and angiotensin II, were not affected by compound 5.

REFERENCES

1. Stewart, J. and Vavrek, R., U.S. Pat. No. 4,801,613
2. Stewart, J. and Vavrek, R., U.S. Pat. No. 4,693,993
3. Breipohl, G., Henke, S., Knolle, J., Hock, F., and Scholkens, B., European Patent Application No. 0 455 133 A2
4. Kyle, D., PCT Application No.: PCT/US92/10469
5. Kyle, D., PCT Application No.: PCT/US92/03031
6. Kyle, D., PCT Application No.: PCT/US92/03033
7. Young, D. et al, Synthesis of Bradykinin Analogs Containing N-Benzyglycine P357, Thirteenth American Peptide Symposium, Edmonton, Alberta, Jun. 20, 1993
8. Young, D. et al, Use of N-Benzylglycine For the Preparation of Peptide-Peptoid Analogs of Biologically Active Peptides, P323, Thirteenth American Peptide Symposium, Edmonton, Alberta, Jun. 20, 1993
9. Young, D. et al, Use of N-benzylglycine as a Replacement for Aromatic Amino Acid Residues, Proc. 11th American Peptide Symposium, p. 155 (1990)
10. Farmer, S. G. and Burch, R. M., The Pharmacology of Bradykinin Receptors, in *Bradykinin Antagonists*, R. M. Burch, ed., Marcel Dekker, Inc. New York, pp. 1–31, (1991)
11. Griesbacher, T., Lembeck, F., Effect of Bradykinin Antagonists on Bradykinin Induced Plasma Extravasation, Venoconstriction, Prostaglandin E2 Release, and Nociceptor Stimulation and Contraction of the Iris Sphincter Muscle in the Rabbit, *Br. J. Pharmacol.*, 92:333–340 (1987)
12. Taiwo, Y. O. and Levine, J. D., Characterization of the Arachadonic Acid Metabolites Mediating Bradykinin and Noradrenaline Hyperalgesia, *Brain Res.*, 458:402–406 (1988)
13. Steranka, L. R. et al, Bradykinin as a Pain Mediator: Receptors Are Localized to Sensory Neurons, and Antagonists Have Analgesic Actions, *Proc. Nat. Acad. Sci. USA*, 85:3245–3249 (1988)
14. Dray, A., Bettaney, J., Forster, P. and Perkins, M. N., Bradykinin-Induced Stimulation of Afferent Fibres is Mediated Through Protein Kinase C, *Neurosci. Lett.*, 91:301–307 (1988)
15. Steranka, L. R., Farmer, S. G. and Burch, R. M., Antagonists of B2 Bradykinin Receptors, *FASEB J.*, 32019–2025 (1989)
16. Haley, J., Dickenson, A. H. and Schacter, M., Electrophysiological Evidence for a Role of Bradykinin in Chemical Nociception in the Rat, *Neurosci. Lett.*, 97:198–202 (1989)
17. MarCeau, F., Lussier, A., Regoli, D., Giroud, J. P., Pharmacology of Kinins: Their Relevance to Tissue Injury and Inflammation, *Gen. Pharmacol.*, 14:209–229 (1983)
18. Proud, D., Kaplan, A. P., Kinin Formation: Mechanism and Role in Inflammatory Disorders, *Annu. Rev. Immunol.*, 6:49–84 (1988)
19. Colman, R. W., Wong, P. Y., Kallikrein-Kinin System in Pathologic Conditions, in *Bradykinin, Kallidin and Kallikrein, Handbook of Experimental Pharmacology*, Vol. 25, Erdos, E. G. ed., Springer Verlag, New York (1979)
20. Greaves, M. W., Inflammation and Mediators, *Br. J. Dermatol.*, 119:419–426 (1988)
21a. Martinez-Brotons, F., Oncins, J. R., Mestres, J., Amargos, V., Reynaldo, C., Plasma kallikrein-kinin system in patients with uncomplicated sepsis and septic shock—comparison with cardiogenic shock., *Thrombosis and Haemostasis*, 58:709–719 (1978)
21b. Whalley, E. T., Solomon, J. A., Modafferi, D. M., Bonham, K. A., Cheronis, J. C., CP-0127, a novel potent bradykinin antagonist, increases survival in rat and rabbit models of endotoxin shock, *Agents and Actions*, 38:413–420 (1992)
22. Farmer, S. G., Airway Pharmacology of Bradykinin and Abraham, William M., Bradykinin Antagonists in a Sheep model of allergic Asthma, in *Bradykinin Antagonists*, R. M. Burch, ed., Marcel Dekker, Inc., New York, pp. 213–236 and 261–276 (1991)
23. Untenberg, A., Dautermann, C., Baethemann, A., Muller-Esterl, W., The kallikrein—kinin system as mediator in vasogenic brain edema—Part 3: Inhibition of the kallikrein-kinin system in traumatic brain swelling, *J. Neurosurgery*, 64:269–276 (1986)
24. Holder, L. A. and Neely, A. N., Hagerman Factor-dependent Kinin Activation in Burns and Its Theoretical Relationship to Postburn Immunosuppression Syndrome and Infection, *Journal of Burn Care and Rehabilitation*, 11:496503 (1990)
25. Sicuteri, F., Vasoneuroactive Substances and Their Implication in Vascular Pain, *Res. Clin. Stud. Headache*, 1:6 (1967)
26. Cheronis, J. C., Whalley, E. T., Nguyen, K. T., Eubanks, S. R., Allen, L. G., Duggan, M. J., Loy, S. D., Bonham, K. A. and Blodgett, J. K., A New Class of Bradykinin Antagonists: Synthesis and In Vitro Activity in Bissuccinimidoalkane Peptide Dimers, *J. Med. Chem.*, 1563–1572 (1992)
27. Dray, A. and Bevan, S., *TIPS*, 14 287 (1993)
28. Stewart, J. M. and Young, J. D., *Solid Phase Peptide Synthesis*, Pierce Chemical Company, (1984)
29. Bodanszky, M. and Bodanszky, A., The Practice of Peptide Synthesis, Springer Verlag, 1984. Miklos Bodansky, *Principles of Peptide Synthesis*, Springer Verlag, (1984)
30. Barany, G. et al, Solid Phase Peptide Synthesis, A Silver Anniversary Report, *Int. J. Peptide Protein Res.* 30:705739 (1987)
31. Tung, R. D., Rich, D. H., Dhaoan, M., *J. Am. Chem. Soc.* 107 4342 (1985)
32. Coste, J., Peptides: Proceedings of the Twenty-first European Peptide Symposium (1990)
33. Beyermann, M.; Bienert, M.; Niedrich, H.; Casrpino, L. A.; Sadat-Aalaee, D. Rapid Continuous Peptide Synthesis via FMOC Amino Acid Chloride Coupling and 4-(Aminomethyl)piperidine Deblocking, *J. Org. Chem.* 55, 721–728, (1990)
34. Carpino, L. A., Sadat-Aalaee, D., Chao, H. G., DeSelms, R. H., *J. Am. Chem. Soc.* 112 9652 (1990)
35. Zuckermann, R. N., *J. Am. Chem. Soc.* 114 10646 (1992)
36. T. Greene and P. G. M. Wuts provide examples of numerous protecting groups which are compatible with common techniques applied in peptide synthesis., Greene, T., Wuts, P. G. M., *Protective Groups in Organic Synthesis*, second edition, John Wiley and Sons, (1991)

37 Bundgaard, H., *Design of Prodrugs*, Elsevier (1985)

38 Reference 28, p. 105–107

39 Porter, T. H. and Shive, W., *J. Med. Chem.* 11 402 (1968)

40 Hill, J. THill, J. T. and Dunn, F. W., *J. Org. Chem.* 30 1321 (1965)

41 ABI 431 Fmoc Procedure, *Applied Biosystems Model 431A Peptide Synthesizer User's Manual*, Version 2.0, January 1992

42 Bernatowicz, M. S., Matsueda, G. and Wu, Y., *J. Org. Chem* 57 2497 (1992)

43 Arunlakshana, O., Schild, H. O., *Br. J. Pharmacology* 14 48–58 (1959)

44 Booth, A. G. and Kenny, A. J., *Biochemical Journal* 142, 575–581 (1974)

45 Erdos, E. G., Johnson, A. R., Skidgel, R. A., *Biochemical Pharmacology* 33 3471–3478 (1984)

We claim:

1. A peptide of the formula:

$Z'-Z^0-A^1-B^2-C^3-D^4-E^5-F^6-G^7-H^8-I^9$ wherein

Z' is hydrogen, acetyl, adamantylcarboxyl or adamantylacetyl or is absent;

$Z^0$ is a direct bond, hydrogen, D or L-Arg, D or L-Lys, D or L-ornithine, or δ-Gpa or is absent;

$A^1$ is D or L-Arg, D or L-Lys, D or L-ornithine, or δ-Gpa;

$B^2$ is Pro, Hyp, sarcosine, Ser, Thr or Gly;

$C^3$ is Hyp, Pro, sarcosine or Gly;

$D^4$ is Gly, Ala or Thi;

$E^5$ is Phe, Igl or Thi;

$F^6$ Ser or Cys;

$G^7$ is DTic, Igl, DPhe or an N-substituted glycine residue selected from NBng, DNBng or DCpg;

$H^8$ is Oic or an N-substituted glycine residue selected from NChg, NCpg, NPhg or $(C_1-C_{12})$alkyl substituted NChg; and $I^9$ is absent or Arg; provided that at least one of $G^7$ or $H^8$ is an N-substituted glycine residue.

2. The bradykinin antagonist of claim 1 wherein
$G^7$ is DTic; and
$H^8$ is NChg, NCpg, or NPhg.

3. The bradykinin antagonist of claim 2 of the formula:

D-Arg-Arg-Pro-Hyp-Gly-Thi-Ser-DTic-NChg-Arg.

4. The bradykinin antagonist of claim 2 of the formula:

δ-Gpa-Arg-Pro-Hyp-Gly-Thi-Ser-DTic-NChg-Arg.

5. The bradykinin antagonist of claim 2 of the formula:

D-Arg-Arg-Pro-Hyp-Gly-Thi-Ser-DTic-NPhg-Arg.

6. The bradykinin antagonist of claim 1 of the formula:

D-Arg-Arg-Hyp-Hyp-Gly-Thi-Ser-DTic-NChg-Arg;

D-Arg-Arg-Pro-Hyp-Gly-Thi-Ser-DTic-NCpg-Arg;

D-Arg-Arg-Pro-Hyp-Gly-Igl-Ser-DTic-NChg-Arg;

D-Arg-Arg-Pro-Hyp-Gly-Phe-Ser-DTic-NChg-Arg;

D-Arg-Arg-Pro-Hyp-Gly-Thi-Ser-NBng-Oic;

D-Arg-Arg-Pro-Hyp-Gly-Thi-Ser-DPhe-NChg-Arg;

D-Arg-Arg-Pro-Hyp-Gly-Thi-Ser-DCpg-NChg-Arg;

D-Arg-Arg-Pro-Hyp-Gly-Thi-Ser-DPhe-NPhg-Arg;

D-Arg-Arg-Pro-Hyp-Gly-Thi-Ser-DNBng-Oic-Arg;

or

δ-Gpa-Pro-Hyp-Gly-Thi-Ser-DTic-NChg-Arg.

7. A therapeutic method of alleviating pain comprising administering to a patient in need of such treatment, an amount of a bradykinin antagonist of claim 1 effective to reduce said pain.

8. A therapeutic method comprising alleviating the symptoms of asthma by administering to a patient in need of such treatment, an effective amount of a bradykinin antagonist of claim 1.

9. A therapeutic method comprising treating inflammatory bowel disease by administering to a patient in need of such treatment, an effective amount of a bradykinin antagonist of claim 1.

10. A therapeutic method of treating inflammation comprising administering to a patient in need of such treatment, an amount of a bradykinin antagonist of claim 1 effective to reduce said intimation.

11. A method of treating head trauma comprising administering to a patient in need of such treatment, an amount of a bradykinin antagonist of claim 1 effective to reduce cerebral edema associated with said head trauma.

12. A method of treating cardiovascular dysfunction comprising administering a therapeutically effective amount of the compound claim 1.

13. The method of claim 12, wherein the cardiovascular dysfunction consist of ischemia, vessel damage or cardiovascular tissue damage.

* * * * *